(12) United States Patent
Gryhorieva et al.

(10) Patent No.: US 12,168,018 B1
(45) Date of Patent: Dec. 17, 2024

(54) PHARMACOLOGICALLY ACTIVE LIPOSOMAL COMPOSITION COMPRISING QUERCETIN AND ZINC

(71) Applicants: CONSORTIUM "UKRINDUSTRY", Kyiv (UA); STATE INSTITUTION INSTITUTE OF PHARMACOLOGY AND TOXICOLOGY OF NATIONAL ACADEMY MEDICAL SCIENCES OF UKRAINE, Kyiv (UA)

(72) Inventors: Ganna Gryhorieva, Kyiv (UA); Nataliia Konakhovych, Vasylkiv (UA); Yurii Krasnopolskyi, Kharkov (UA); Oleksandr Pylypenko, Kyiv (UA); Vitalii Prokhorov, Kharkov (UA); Zinaida Suvorova, Sofiivska Borshchahivka (UA); Oleg Yadlovski, Kyiv (UA)

(73) Assignees: CONSORTIUM "UKRINDUSTRY", Kyiv (UA); STATE INSTITUTION INSTITUTE OF PHARMACOLOGY AND TOXICOLOGY OF NATIONAL ACADEMY MEDICAL SCIENCES OF UKRAINE, Kyiv (UA)

( * ) Notice: Subject to any disclaimer, the term of this patent is extended or adjusted under 35 U.S.C. 154(b) by 0 days.

(21) Appl. No.: 18/399,141

(22) Filed: Dec. 28, 2023

(30) Foreign Application Priority Data

Sep. 14, 2023 (UA) .................................. 2023 04351

(51) Int. Cl.
| | |
|---|---|
| A61K 31/685 | (2006.01) |
| A61K 9/00 | (2006.01) |
| A61K 9/107 | (2006.01) |
| A61K 9/127 | (2006.01) |
| A61K 31/353 | (2006.01) |
| A61K 31/7016 | (2006.01) |
| A61K 33/30 | (2006.01) |
| A61P 11/08 | (2006.01) |

(52) U.S. Cl.
CPC .......... *A61K 31/685* (2013.01); *A61K 9/0019* (2013.01); *A61K 9/0043* (2013.01); *A61K 9/107* (2013.01); *A61K 9/127* (2013.01); *A61K 31/353* (2013.01); *A61K 31/7016* (2013.01); *A61K 33/30* (2013.01); *A61P 11/08* (2018.01)

(58) Field of Classification Search
CPC .................................................. A61K 31/685
See application file for complete search history.

(56) References Cited

U.S. PATENT DOCUMENTS

2017/0196808 A1* 7/2017 Grygor'ieva ........ A61K 31/352

FOREIGN PATENT DOCUMENTS

| | | |
|---|---|---|
| CN | 100367953 C | 2/2008 |
| CN | 100367968 C | 2/2008 |
| CN | 101904821 A | 12/2010 |
| CN | 102058536 A | 5/2011 |
| RU | 2 181 051 C1 | 4/2002 |
| UA | 38504 A | 5/2001 |
| UA | 76393 C2 | 7/2006 |
| UA | 111762 C2 | 6/2016 |
| WO | 2011/019677 A1 | 2/2011 |

OTHER PUBLICATIONS

Feldman, C., et al., "Epidemiology of lower respiratory tract infections in adults," Expert Review of Respiratory Medicine, 2019, 13(1):1-16.
Glezen, W.P., et al., "Epidemiology of Acute Lower Respiratory Disease in Children," The New England Journal of Medicine, 1973, 288(10):498-505.
Rom, W.N., et al., "Characterization of the Lower Respiratory Tract Inflammation of Nonsmoking Individuals with Interstitial Lung Disease Associated with Chronic Inhalation of Inorganic Dusts," Am Rev Respir Dis, 1987, 136:1429-1434.
Meyer, N.J., et al., "Acute respiratory distress syndrome," Lancet, 2021, 398:1-17.
Miller, K., "Acute Respiratory Distress Syndrome (ARDS)". WebMD. [retrieved on Nov. 23, 2023]. Retrieved from the Internet <URL: https://www.webmd.com/lung/ards-acute-respiratory-distress-syndrome>, pp. 1-3.
Meftahi, G.H., et al., "A Vicious Circle Between Oxidative Stress and Cytokine Storm in Acute Respiratory Distress Syndrome Pathogenesis at COVID-19 Infection," Ukr. Biochem. J., 2021, 93(1):18-29.

(Continued)

*Primary Examiner* — Rei Tsang Shiao
(74) *Attorney, Agent, or Firm* — Saliwanchik, Lloyd & Eisenschenk

(57) ABSTRACT

The invention relates to pharmaceutics and concerns a pharmacologically active liposomal composition comprising quercetin and zinc. According to the invention, the composition further comprises zinc chloride, while including a zinc ion into liposomes, and the composition is a lyophilized powder in the following ratio of components (wt. %):

quercetin 1
phosphatidyl choline 36.7
zinc ion 0.11-0.43
lactose 54.51
remainder—water, chloride ion.

Therewith, the content of liposomes has the following ratio:
phosphatidylcholine:quercetin:zinc ion—1:0.027:0.002-1:0.027:0.023.

The claimed composition possesses anti-inflammatory effect and may be used as a pharmacotherapeutical agent in acute respiratory distress syndrome in a form of emulsion for inhalation and/or injection use.

4 Claims, 16 Drawing Sheets

(56) References Cited

OTHER PUBLICATIONS

Mahmudpour, M., et al., "COVID-19 cytokine storm: The anger of inflammation," Cytokine, 2020, 133(155151):1-10.

Empson, S., et al., "COVID-19 Acute Respiratory Distress Syndrome: One Pathogen, Multiple Phenotypes," Crit Care Clin, 2022, 38:1-16.

Lai, C., et al., "Asymptomatic carrier state, acute respiratory disease, and pneumonia due to severe acute respiratory syndrome coronavirus 2 (SARS-CoV-2): Facts and myths," Journal of Microbiology, Immunology and Infection, 2020, 53:1-10.

Acute Respiratory Distress Sydrome, What Is Acute Respiratory Distress Syndrome? (a forum for National Heart, Lung, and Blood Institute) [online]. NIH, National Heart, Lung, and Blood Institute, Mar. 24, 2022, [retrieved on Apr. 26, 2024]. Retrieved from the Internet: <https://www.nhlbi.nih.gov/health/ards>, pp. 1-4.

Nijveldt, R.J., et al., "Flavonoids: a review of probable mechanisms of action and potential applications," Am J Clin Nutr, 2001, 74:418-425.

Read, M.A., "Flavonoids: Naturally Occurring Anti-Inflammatory Agents," American Journal of Pathology, Aug. 1995, 147(2):235-237.

Bischoff, S.C., "Quercetin: potentials in the prevention and therapy of disease," Current Opinion in Clinical Nutrition and Metabolic Care, 2008, 11:733-740.

Ganesan, S., et al., "Quercetin inhibits rhinovirus replication in vitro and in vivo," Antiviral Research, 2012, 94:1-15.

Biancatelli, R.M.L.C., et al., "Quercetin and Vitamin C: An Experimental, Synergistic Therapy for the Prevention and Treatment of SARS-CoV-2 Related Disease (COVID-19)," Frontiers in Immunology, Jun. 19, 2020, 11(1451):1-11.

Quercetin (Quercetinum). Datasheet. [online]. Compendium, 2023 [retrieved on Nov. 24, 2023]. Retrieved from the internet: <https://compendium.com.ua/dec/260462/>.

Tiwari, G., et al., "Drug delivery systems: An updated review," International Journal of Pharmaceutical Investigation, Jan. 2012, 2(1):1-10.

Barbosa Da Silva, W.M., et al., "Synthesis of Quercetin-Metal Complexes, In Vitro and In Silico Anticholinesterase and Antioxidant Evaluation, and In Vivo Toxicological and Anxiolitic Activites," Neurotoxicity Research, Dec. 18, 2019, pp. 1-11.

Shastrala, K., et al., "Synthesis, characterization, and pharmacological evaluation of some metal complexes of quercetin as P-gp inhibitors," Future Journal of Pharmaceutical Sciences, 2021, 7(99):1-13.

Clergeaud, G., et al., "A simple liposome assay for the screening of zinc ionophore activity of polyphenols," Food Chemistry, 2016, 197:916-923.

Prasad, A.S., "Discovery of Zinc for Human Health and Biomarkers of Zinc Deficiency," Molecular, Genetic, and Nutritional Aspects of Major and Trace Minerals, 2017, pp. 1-21.

Uskokovic-Markovic, S., et al., "Zinc-quercetin complex—from determination to bioactivity," Acta Agriculturae Serbica, 2020, 25(50):113-120.

Corvitin ® (Corvitin®). Datasheet. [online]. Compendium, 2023 [retrieved on Nov. 24, 2023]. Retrieved from the internet: <https://compendium.com.ua/dec/281727/>.

Pomytkin, I.A., et al., "A Model of Fatal Acute Lung Injury and Acute Respiratory Distress Syndrome," Journal Biomed, 2020, 16(4):24-33 (abstract only).

"Liposomal praeperationes," The State Pharmacopoeia of Ukraine 2.0, 2015, pp. 1-9.

Priprem, A., et al., "Anxiety and cognitive effects of quercetin liposomes in rats," Nanomedicine: Nanotechnology, Biology, and Medicine, 2008, 4:1-10.

Lipoflavon (Lipoflavon). Datasheet. [online]. Compendium, 2023 [retrieved on Nov. 24, 2023]. Retrieved from the internet: <https://compendium.com.ua/dec/268166/>.

"Buffer Calculations," The State Pharmacopoeia of Ukraine, 2001, pp. 1-3.

European Convention on the Protection of Vertebrate Animals Used for Research and Other Scientific Purposes, Council of Europe, Mar. 18, 1986 [online] Retrieved from the internet: <https://zakon.rada.gov.ua/laws/show/994_137#Text>, pp. 1-18.

Stefanov, O.V., "Experimental (Preclinical) Study: The "colloquial" language is used to describe the non-steroidal anti-inflammatory drugs," Avicenna, 2001, pp. 1-534.

Zhang, Y., et al., "Extracellular Histones Play an Inflammatory Role in Acid Aspiration-induced Acute Respiratory Distress Syndrome," Anesthesiology, Jan. 2015, 122(1):127-139.

\* cited by examiner

PHARMACOLOGICALLY ACTIVE LIPOSOMAL COMPOSITION COMPRISING QUERCETIN AND ZINC

CROSS-REFERENCE TO RELATED APPLICATION

This application claims priority to Ukrainian Application No. a 2023 04351, filed Sep. 14, 2023, which is hereby incorporated by reference in its entirety.

The invention relates to pharmaceutics and concerns a pharmacologically active liposomal composition comprising quercetin and zinc, has an anti-inflammatory effect and may be used as a pharmacotherapeutic agent in acute respiratory distress syndrome.

Usually, epidemiological analysis defines lower respiratory tract diseases as serious medical issues having life-threatening consequences [1-3], among which a special role is taken by a so-called "Acute respiratory distress syndrome"-ARDS. ARDS is a clinically heterogeneous syndrome that may occur in various pathological conditions (pneumonia, aspiration, injure, sepsis) in wide range of clinical manifestations [4, 5]. ARDS which is based on a diffuse inflammation of lungs with an acute respiratory failure is manifested as an acute hypoxemia and bilateral infiltrations of chest which are caused by a non-cardiogenic pulmonary edema [4]. A dangerous developmental factor of the ARDS is a non-controlled discharge of pro-inflammatory mediators which is called "cytokine storm" that results in serious damages of endothelium of capillaries and alveoli, development of pulmonary hypertension and hemorrhages [6, 7].

Heavy worldwide experience of unprecedented spread of the ARDS during the COVID-19 pandemic [8, 9] brought light on main medical challenges which are associated with this syndrome: "unacceptably high mortality and insufficient efficiency of existing pharmacotherapy" [3].

Strategy of treatment of the ARDS implies combining an artificial pulmonary ventilation and a so-called maintenance drug therapy which still has a predominantly empiric nature [3, 10]. Considering a wide variability of used drugs (agents for correcting pulmonary vasodilatation, coagulation, stabilization of epithelium, recovery of alveolar units, enhancement of clearance of liquid and acid etc.), a permanent component of the ARDS pharmacotherapy is anti-inflammatory agents of steroid and non-steroid nature. At the background of the typically serious condition of patients with ARDS, such polypragmasy has focused attention on risks of maintenance therapy as a result of known and unexpected adverse reactions of individual drugs and their mutual influence. Attempts to increase a benefit-risk balance when treating the ARDS and to reduce volumes of so-called "risky therapy" [3] actualize a demand in safe drugs having polyfunctional pharmacological effects.

Among these agents, attention is drawn to quercetin (QC) 3,3',4',5,7-pentaoxyflavone being a natural polyphenol that belongs to a subclass of flavonoids [11]. High antioxidant activity of the QC defines polyfunctionality of its pharmacotherapeutic potential: anti-inflammatory, thrombin-inhibiting, antispastic effect etc. [11-13] which is especially important in the context of activation of inflammatory cascade and blood coagulation system that is accented in ARDS. Considering the ARDS spread during the coronavirus disease as a result of SARS-COV-2 infection, a predicted in vitro and in silico [14, 15] anti-virus effect of the QC should be noted as well.

Nevertheless, the fact that the QC is almost non-soluble in physiologically adequate systems drastically restricts a range of its drugs to almost only oral forms having a low bioavailability of active substance [13,16], which a priori makes their use impossible in serious diseases with a destroyed compliance of the patients.

Expediency of pharmacotherapeutic use of polytropic properties of the QC for treatment of ARDS brings attention to its products which, as predicted, are suitable for methods for administration into a body and their combining which are alternative to the oral method. These requirements may be met by transport forms of the QC being an active ingredient in a certain vehicle, according to a modern pharmacy narrative "Drug delivery systems" [17].

Transport QC compositions are described, the compositions are in a form of a solution with polyvinylpyrrolidone or a mixture of sodium tetraborate and Trilon B or a suspension with a number of acidifiers, flavorings and colorants [20]. A common drawback of these compositions is a presence of predominant amounts of exogeneous excipients and instability which deteriorates usability and safety of a potential parenteral administration.

It should be noted that among transport forms of natural polyphenols, in particular QC, compositions with essential metals (zinc, copper, iron) are considered, where the flavonoid acts as an ionophore [21,22]. It has been in vitro demonstrated that complex formation, in particular, with a zinc cation facilitates passage of QC through a model cellular membrane that is imitated by a monolayer liposome [23]. Of course, establishment of transport role for the QC-Zn complex expands the understanding of important physiological status of this biometal [24, 25], but there is still no information about pharmacologically identified systems of QC with zinc which could have a predicted clinical translation. Opportunely it should be noted that nowadays, therapeutic use of zinc compounds is restricted by oral products having a status of so-called "biological supplements".

A composition of QC in a vehicle being povidone (polyvinylpyrrolidone) in a presence of sodium hydroxide is known, the composition is in a form of a lyophilized powder for preparing a solution for injections/infusions [26]. This composition is introduced as a licensed drug "Corvitin" for a complex therapy of cardiovascular diseases and cerebral circulation disturbances. There is no information regarding suitability of the QC-povidone composition for use in ARDS. Predicted warning of such use is caused by described consequences of side effect of injection and inhalation administration of povidone as a QC matrix (possible development of pulmonary interstitial fibrosis, reticulocytosis, anemia, leukocytosis) [27, 28].

According to normative documents of regulatory authorities, innovations of modern pharmacy include drug delivery systems on a liposomal platform [29]. Developments of more than 70 worldwide licensed liposomal drugs and vaccines (including a vaccine against Covid-19 by Pfizer-BionTech and Moderna) based on liposomal compositions also concern liposomal products comprising QC.

Liposomal compositions of QC are known which are based on the following phospholipid vehicles: phosphatidyl choline (PC) and its mixtures with phosphatidyl choline ethanolamine or phosphatidyl choline ethanolamine distearate in a presence of a number of additives (cholesterol, hydroxypropyl cyclodextrin, polyethyleneglycol, stearic acid or glycerol) [30-33]. Also, a composition of QC with "a surrogate surfactant" is described, which, in contrast to an endogenous surfactant, comprises an artificial mixture of PC with variations of surfactant additives and sorbents (tween-80, deoxycholate, polyethylenized castor oil, poloxamer, methyl cellulose etc.) [34].

A common drawback of these compositions of QC with phospholipids is a presence of a large range of additives of various (sometimes incompatible) chemical nature. This factor that generally contradicts the Occam's razor ("Essences must not be multiplied"), in the context of said compositions, negatively affects the uniformity of phase condition, dispersiveness of particles and stability up to destruction of the liposomal structure. When combined with a non-physiological nature of part of components, this factor puts functionality and safety of parenteral methods of administration of these compositions in a doubt. This could explain the fact that none of the mentioned phospholipid QC products came closer to the status of the drug having a proven effect, safety and pharmaceutical quality.

Methods for preparing a QC composition in phosphatidyl choline liposomes in a form of a lyophilized powder in a presence of lactose are described [35, 36]. This composition forms the base for a licensed drug "Lipoflavone" [37]. Lipoflavone in a form of a solution for injections/infusions that is prepared from the lyophilized composition is used as a cardioprotector in cardiological (acute myocardial infarction, angina pectoris) and in oncological clinic (cardiomyopathy caused by a polychemotherapy of breast cancer). In ophthalmologic clinic, treatment effect of eye drops of Lipoflavone in keratitis, eye injuries and burns has been established.

A liposomal composition of QC and PC prepared according to Patent of Ukraine No. UA 111762 is taken as the closest prior art of the claimed subject matter of the invention being a composition that is the closest one in terms of a set of features, namely: a nature of majority of components of the composition and liposomal form of the product that comprises QC and has pharmacological activity.

The liposomal composition of QC and PC, according to the prototype, is characterized by a mass ratio of PC:QC therein (1:0.020-0.050) and parameters of the liposomal entity (sizes and fineness of dispersion of particles of liposomes, stability of the reconstituted emulsion, % of inclusion of the QC to liposomes). Lactose content of the composition is not fixed, but it may be evaluated according to quantitative parameters of the preparation process according to and upon analysis of the prototype after its reproduction in order to establish competitiveness of the claimed subject matter.

There is no information about functional correspondence of the prototype composition to the treatment of the ARDS and its suitability for inhalation administration which may be crucially important when respiratory organs are affected. Although this "information lacuna" does not compromise general pharmaceutical usage of the prototype, it is expedient for the pharmacotherapy of the ARDS to be oriented towards novel liposomal QC products having a potentially high functionality at various administration routes.

A task of the claimed invention is to provide a liposomal composition of QC having a high pharmaceutical quality which exhibits pharmacological activity at ARDS and exhibits anti-inflammatory effect at various modes of administration to the body.

SUMMARY OF THE INVENTION

The posed task is resolved by providing a liposomal composition in a form of a lyophilized powder that comprises phosphatidyl choline, quercetin, lactose and further comprises a zinc ion that is achieved by adding zinc chloride to the composition to introduce the zinc ion into the liposomes. An embodiment of the subject invention is characterized in that it has the following ratios of components (wt. %):

quercetin—1,
phosphatidyl choline—36.7,
zinc ion—0.11-0.43,
lactose—54.51,
the remainder—water, chloride ion, wherein a ratio of mass fractions of phosphatidyl choline: quercetin:zinc ion in the liposomes is in a range from 1:0.027:0.002 to 1:0.027:0.023.

The subject invention exhibits pharmacological activity in ARDS upon intravenous and inhalation administration and possesses an anti-inflammatory effect.

DETAILED DESCRIPTION

Examples provided hereinafter illustrate preparation of the target composition product as well as the prototype composition for comparison.

Example 1—Exemplary embodiment of the subject invention. A weighed amount 1.25 g of QC (based on 100% substance [e.g., 38.39]) is dissolved in 125 ml of ethyl alcohol while stirring. A weighed amount 42.0 g of PC (based on 100% substance [e.g., 40.41]) is dissolved in 150 ml of ethyl alcohol and added to the QC solution. A mixture of solutions is transferred to the rotary evaporator and the solvent is removed under vacuum at a temperature of 40-42° C. until a thin film is produced. After completion of a drying process, an inert gas is transmitted to a flask of an evaporator during 20 min.

The produced film is quantitatively taken off from the flask walls of the evaporator by means of 1400 ml of a lactose solution (pharmacopeial milk sugar) in the pH phosphate buffer (6.7-7.1) comprising 50.0 g of lactose under stirring during 10 min at 10 RPM until a homogeneous emulsion is produced. 50 ml of a zinc chloride solution (e.g., [43]) in a pH phosphate buffer (6.7-7.1) comprising 0.545 g of zinc chloride (based on 100% substance $ZnCl_2$) or 0.262 g of zinc ion (based on $Zn^{2+}$) is added to the produced mixture and stirred for 5 min at 10 RPM.

The emulsion is subjected to dispersing in a high-pressure homogenizer (e.g., M 110P Microfluidizer Processor, Microfluidics) at a temperature 38-43° C. with a stepwise pressure increase from 300 atm to 900 atm in 1-9 cycles. At the end of dispersing process, size of particles of the emulsion (e.g., Malvern Zetasizer Nano S) is not greater than 180 nm.

After homogenization, 50 ml of the lactose solution in a pH phosphate buffer (6.7-7.1) comprising 12.5 g of lactose is added to the emulsion and stirred for 5 min at 10 RPM. The produced emulsion is filtered through a membrane having a pore diameter of 0.22 µm, subjected to sterilization filtration and poured in doses into glass bottles in aseptic conditions. The bottles with emulsion are subjected to intensive freezing and lyophilizing drying is conducted (e.g., Martin Christ-2-6-D, USA). Upon drying, the bottles with the lyophilized product are sealed under the inert gas atmosphere in aseptic conditions. The bottles with the lyophilized product are stored at a temperature of −(18-20)° C.

In Examples 2-5, embodiments of the subject invention were prepared according to the description of Example 1. Changes are reflected in Table 1.

TABLE 1

Components for preparation of the
claimed composition and the prototype composition

| | Example No. | | | | | |
|---|---|---|---|---|---|---|
| | The claimed composition | | | | | The prototype composition |
| The used components | 1 | 2 | 3 | 4 | 5 | 6 |
| QC: | | | | | | |
| weight, g | 1.25 | 1.25 | 1.25 | 1.25 | 1.25 | 1.25 |
| solution volume, ml | 125 | 125 | 125 | 125 | 125 | 125 |
| PC: | | | | | | |
| weight, g | 42.0 | 42.0 | 42.0 | 42.0 | 42.0 | 42.0 |
| solution volume, ml | 150 | 150 | 150 | 150 | 150 | 150 |
| Lactose: | | | | | | |
| Before dispersing: | | | | | | |
| weight, g | 50.0 | 50.0 | 50.0 | 50.0 | 50.0 | 50.0 |
| solution volume, ml | 1400 | 1370 | 1410 | 1430 | 1300 | 1450 |
| After dispersing: | | | | | | |
| weight, g | 12.5 | 12.5 | 12.5 | 12.5 | 12.5 | 12.5 |
| solution volume, ml | 50 | 50 | 50 | 50 | 50 | 50 |
| Zinc chloride, $ZnCl_2$: | | | | | | |
| weight, g | 0.545 | 1.090 | 0.273 | 0.136 | 2.180 | Absent |
| solution volume, ml | 50 | 80 | 40 | 20 | 150 | |
| *incl.: | | | | | | |
| ion $Zn^{2+}$, g | 0.262 | 0.523 | 0.131 | 0.066 | 1.046 | |
| ion $Cl^-$, g | 0.283 | 0.567 | 0.141 | 0.070 | 1.134 | |

*calculated according to the formula of $ZnCl_2$ molecule (m.m. 136.28)

The target product is a lightweight amorphous light-yellow powder having a distinctive odor that is provided in the bottle.

Preparation of another embodiment of the subject invention according to is described in Example 6. Identical reagents, solvents and equipment are used both for the claimed composition and the prototype.

Example 6—The prototype composition. A weighed amount 1.25 g of QC (based on 100% substance) is dissolved in 125 ml of ethyl alcohol while stirring. A weighed amount 42.0 g of PC (based on 100% substance) is dissolved in 150 ml of ethyl alcohol and added to the QC solution. A mixture of solutions is stirred, transferred to the rotary evaporator and the solvent is removed under vacuum at a temperature of 40-42° C. until a thin film is produced. After completion of a drying process, an inert gas is transmitted to a flask of an evaporator during 20 min. The film is quantitatively taken off from the flask walls of the evaporator by means of 1450 ml of a lactose solution in the pH phosphate buffer (6.7-7.1) comprising 50.0 g of lactose under stirring during 10 min at 10 RPM until a homogeneous emulsion is produced.

The emulsion is subjected to dispersing in a high-pressure homogenizer at a temperature 38-43° C. with a stepwise pressure increase from 300 atm to 900 atm in 1-9 cycles. At the end of dispersing process, size of particles of the emulsion is not greater than 180 nm. After homogenization, 50 ml of the lactose solution in a pH phosphate buffer (6.7-7.1) comprising 12.5 g of lactose is added to the emulsion and stirred for 5 min at 10 RPM. The produced emulsion is filtered through a membrane having a pore diameter of 0.22 μm, subjected to sterilization filtration and poured in doses to glass bottles in aseptic conditions. The bottles with emulsion are subjected to intensive freezing and lyophilizing drying is conducted. The bottles with the lyophilized product are sealed under the inert gas atmosphere in aseptic conditions.

The prototype composition is provided in the bottle in a form of a lightweight amorphous light-yellow mass having a lemon tone and a distinct odor.

During identification and establishing the formulation of the embodiments of liposomal composition and the prototype composition, they were used in a form of a lyophilized powder, as well as emulsion reconstituted from the lyophilized product in a sterile isotonic 0.9% solution of sodium chloride at a temperature of 37-40° C. which corresponds to a form of a potential pharmacotherapeutic usage.

Formulation and pharmaceutical quality of the produced embodiments of liposomal composition are established according to results of qualitative and quantitative identification of components (QC, PC, lactose, zinc) and confirmation of the liposomal status and stability using a number of independent physical and chemical methods, namely:

by a spectrophotometric method according to a characteristic absorption at wavelengths (255-259) nm and (373-377) nm and an optical density value (375±2) nm (включити (490±2) nm) of the product solution in ethyl alcohol as compared to the one of the standard quercetin sample solution (identification and quantitative determination of QC, respectively);

by an atomic adsorption spectroscopy (spectrometer Shimadzu AA-6300 having a gas-discharge lamp (current 6-10 mA) by measuring an atomic absorption of the composition after transition into a gaseous phase at 2000° C. in an air/acetylene flame at an emission wave of 213.9 nm. For calibration, zinc cyclohexane butyrate is used as a standard (identification and quantitative determination of zinc).

by a thin-layer chromatography method on plates Supelco Silicagelon TLC Al according to a chromatogram of the target product solution in a mixture of chloroform, methanol and water (73:23:3 vol.) on which dots of PC are present at a level of main dots on the chromatogram of the solution of the standard PC sample (identification of PC);

by a liquid chromatography method with an evaporative light scattering detection (ELSD) on a PerfectCHrom 100 Diol column according to a chromatogram of the target product solution in the mixture of chloroform and methanol (20:80 vol.), while using, for calibration and comparison, the solutions of standard PC samples (identification and quantitative determination of PC);

by a method of iodometric chemical analysis by precipitation of the target product emulsion by means of a cuprum sulfate solution in an alkaline medium, contacting a supernatant solution with iodine and titrating a residual iodine by a sodium thiosulfate (identification and quantitative determination of lactose);

by a liquid chromatography method on a SupelcoSi column having a protective cartridge according to product emulsion chromatograms before and after gel permeation chromatography on a Sephadex G-25 column with a control of liposomes discharge at an absorption at 540 nm. Peak area on a standard chromatogram is used for calibration and comparison (control of introduction of components into the liposomes);

by a thin-layer chromatography method on plates Supelco Silicagelon TLC Al according to a chromatogram of the target product solution in a mixture of methanol and water (80:20 vol.) on which dots of lisoderivatives of PC are present at a level of main dots on the chromatogram of the solution of the standard lisoPC sample (identification of PC) using water as a mobile phase (determination of PC oxidation index and liposomes stability);

by a gas chromatography method on a DB-624 column having a peak area of ethyl alcohol on a target product chromatogram having an internal standard (mixture of N,N-dimethylformamide and propanol-1) as compared to a peak on a chromatogram of a standard sample of ethyl alcohol (determination of residual organic solvent);

by a method of laser diffraction of liposomal product emulsion on a Malvern Zetasizer NanoZS device (determination of size of liposomes and their distribution according to the sizes);

determination of pH of the liposomal product emulsion (compliance with requirements of parenteral administration).

Table 2 provides results of physical and chemical analyses.

TABLE 2

Identification of the claimed liposomal composition and the prototype composition according to the data of physical and chemical analyses

| | Example No. | | | | | |
|---|---|---|---|---|---|---|
| | The claimed composition | | | | | The prototype composition |
| Parameter | 1 | 2 | 3 | 4 | 5 | 6 |
| Quantitative identification of the components: | | | | | | |
| QC | + | + | + | + | + | + |
| PC | + | + | + | + | + | + |
| Lactose | + | + | + | + | + | + |
| Zinc | + | + | + | + | + | Absent |
| Quantitative content of the component in the emulsion reconstituted from the lyophilized composition bottle[1], mg/ml: | | | | | | |
| QC (±0.02) | 0.75 | 0.75 | 0.75 | 0.75 | 0.75 | 0.75 |
| PC (±0.15) | 27.50 | 27.50 | 27.50 | 27.50 | 27.50 | 27.50 |
| Lactose (+0.2) | 40.9 | 40.9 | 40.9 | 40.9 | 40.9 | 40.9 |
| Zinc ((+0.002) | 0.16 | 0.33 | 0.08 | 0.04 | 0.32 | Absent |
| Quantitative content of the components in the lyophilized composition, mg/bottle | | | | | | |
| QC (±0.02) | 15.03 | 15.02 | 15.02 | 15.03 | 15.05 | 15.0 |
| PC (±0.15) | 550.3 | 550.2 | 550.3 | 550.4 | 550.2 | 550.1 |
| Lactose (±0.2) | 818.0 | 818.0 | 818.0 | 818.0 | 818.0 | 818.0 |
| Zinc ((±0.002) | 3.202 | 6.505 | 1.641 | 0.832 | 12.804 | Absent |

TABLE 2-continued

Identification of the claimed liposomal composition and the prototype composition according to the data of physical and chemical analyses

| | Example No. | | | | | |
|---|---|---|---|---|---|---|
| | The claimed composition | | | | | The prototype composition |
| Parameter | 1 | 2 | 3 | 4 | 5 | 6 |
| Mass ratio of the components in the lyophilized composition (c.u.)[2] | | | | | | |
| QC:PC:Lactose:Zinc | 1:36.7:54.5:0.21 | 1:36.7:54.5:0.43 | 1:36.7:54.5:0.11 | 1:36.7:54.5:0.06 | 1:36.7:54.5:0.89 | 1:36.7:54.5 (Zn is not present) |
| QC:PC:Zinc ratio in the liposomes before/after gel-filtration (weight ratio) | 1:0.027:0.006/ 1:0.027:0.006 | 1:0.027:0.012/ 1:0.028:0.006 | 1:0.027:0.003/ 1:0.027:0.003 | 1:0.027:0.0002/ 1:0.028:0.0002v | 1:0.027:0.024/ 1:0.028:0.023 | 1:0.028:n/m |
| Inclusions to the liposomes (% to the already included): | | | | | | |
| QC | 100 | 100 | 100 | 100 | 100 | 100 |
| Zinc | 100 | 100 | 100 | 100 | 99 | Absent |
| Size of liposomes[1], nm (±5)/% of liposomes having the corresponding size | 180/100 | 190/95 170/5 | 185/90 170/10 | 190/85 170/15 | 188/80 155/5 125/15 | 185/90 170/10 |
| PC oxidation index (c.u.) | 0.20 | 0.22 | 0.21 | 0.20 | 0.25 | 0.23 |
| Residual solvent content (ethyl alcohol), % | 0.02 | 0.03 | 0.02 | 0.02 | 0.03 | 0.02 |
| Emulsion formation duration/emulsion stability before exfoliation, min[1] | 1.5/70 | 1.7/73 | 1.4/70 | 1.2/72 | 1.3/60[3] | 1.7/72 |
| pH of the emulsion[1] | 7.0 | 7.1 | 7.0 | 6.9 | 7.0 | 6.9 |

(+) - positive identification
[1] Determined for the composition that was firstly resonstituted from the lyophilized composition upon addition of 20 ml of sterile isotonic 0.9% sodium chloride solution to the bottle
[2] Mass ratio is calculated based on the determined quantitative content of the components in the lyophilized composition in the bottle. The lyophilized composition comprises, except for the main components, water that is a mandatory factor of formation of the liposomal structure, as well as chloride (zinc counter-ion) and residual solvent
[3] Light precipitate is observed upon emulsion formation Results of the physical and chemical analyses have confirmed individuality and formulation of certain embodiments as a liposomal product that comprises QC, PC, lactose and zinc, namely:

Positive qualitative identification of QC, PC, lactose and zinc that corresponds to these standards confirms preservation of a native nature of the components comprised in the composition;

Accurately established quantitative content of the components defines the mass ratio of QC:PC:Lactose:Zinc in the composition that is 1:36.7:54.5:(0.06-0.89);

Stability of liposomes in the composition emulsion having a size (180±5 nm) at almost monodispersity is accompanied by a low oxidation index of PC;

According to the gel-filtration data, PC, QC and zinc are quantitatively comprised in the liposomes in the composition;

The lyophilized composition is capable of quick forming the emulsion being stable for exfoliation;

pH of the emulsion that is formed from the lyophilized composition corresponds to the physiological parameters in vivo.

Summarized analysis of characteristics of the compositions according to examples 1-5 and the prototype composition confirms their pharmaceutical quality and allows to identify the formulation and liposomal nature. Only for the compositions according to examples 4-5 and the prototype there are minor variations of individual parameters (dispersiveness of the liposomes size, reconstitution and stability of the emulsion, PC oxidation index). It should be separately noted that formation of the light precipitate in the emulsion is peculiar to the composition of example 5 only. In general, such deviations do not reduce the pharmaceutical quality of the products, although they may affect their stability during intended use and storage.

Optimal pharmaceutical quality and potential correspondence to the parenteral administration as defined by the task of the invention is inherent to the liposomal compositions of examples 1-3 having the mass ratio QC:PC:lactose:zinc of 1:36.7:54.5:0.11-0.43.

According to the task of the invention, the quality of the claimed liposomal composition is evaluated according to parameters of the pharmacological activity in ARDS and inflammation models. The selected specificity of preclinical studies corresponds to the task of the invention, as well as means evidentiality of the pharmacological quality of the created composition at various parenteral routes of administration to the body.

According to preliminary evaluations, the subject embodiments and the prototype composition are safe. In order to meet bioethical conditions that recommend to optimize a number of animals in preclinical experiments [44], evaluation of safety was conducted for the composition of examples 3 and 5 and the prototype product. Upon single intravenous administration and upon repeated daily intraperitoneal injections, said products in the form of emulsion have not caused any animals' death, local irritating effect and manifestations of inflammatory reaction for 6 days, have not made any negative influence onto dynamics of body weight, behavioral reaction and parameters of blood formula, have not caused any dystrophic changes of internal organs upon macroscopic examination.

Therefore, according to evaluation of toxicity upon single and repeated administration, the subject embodiments and the prototype composition should be classified as almost safe agents with no evidences of system toxicity which serves as a ground for their safe pharmacotherapeutic use.

Evaluation and comparison of the specific pharmacological effect of the subject embodiments and the prototype composition were conducted in the following experimental models:
1) exudative inflammation that is caused by subplantar administration of a carrageenin solution to white mice (a carrageenin edema model) [45] with evaluation of influence of the composition emulsion onto development of edema of rear feet.
2) ARDS caused by intratracheal instillation of 0.1N of hydrochloric acid into lungs of the white mice (HCl model) [46] with evaluation of influence of the composition onto survival of the animals, clinical performance, body weight dynamics and morphological state of lungs.
3) fatal ARDS that is caused by intratracheal administration of a mixture of lipopolysaccharide, muramylpeptide and Freund adjuvant (LPS model) to the white mice [47] with evaluation of influence of the composition onto survival of the animals, clinical performance and morphological state of lungs and heart.

The pharmacological activity of the compositions was evaluated in groups of mature white mice having a body weight of 20-26 g. In order to minimize the number of animals in highly invasive experiments during determination of the pharmacological activity in the ARDS models, individual illustrative examples of the subject liposomal composition with varying administration routes were used. In order to provide an optimal balance between compliance with the bioethical conditions and reliability of the evaluation of pharmacological activity, the exemplary compositions in the HCl and LPS models of ARDS were selected according to a crossover principle, while all examples 1-5 of the subject embodiments were investigated in the inflammation model. It should be noted that the pharmacological effect of the prototype composition was investigated in all experimental models (Example 6).

ARDS in the HCl model was reproduced by intratracheal instillation of 0.1N of hydrochloric acid (pH 1.5) in experimental group with 7 animals per each group (n=7).

ARDS according to the LPS model was reproduced by intratracheal administration of a mixture of lipopolysaccharide E. coli (150 µg/mouse), muramylpeptide (50 µg/mouse) and Freund adjuvant (10 µl/mouse) (n=7).

Before induction of ARDS in the HCl and LPS models, the animals were subjected to anesthesia by 1% solution of propofol (0.1 ml/mouse, intravenously). Comparison groups (control-pathology) were constituted by mice which were intratracheally administered with a sterile saline solution.

According to the task of the invention, pharmacological quality of the liposomal composition when treating ARDS was evaluated while varying parenteral administration routes according to the following schemes: a) one intravenous injection immediately before reproduction of the model followed by 1 injection per each 24 hours for 6 days; b) one inhalation 2 hours before reproduction of the model, next inhalations one time per day with 24 hours interval during 6 days; c) one intravenous injection immediately before reproduction of the model following by one inhalation 2 hours after reproduction of the model, next inhalations one time per day with 24 hours interval during 6 days.

The exudative inflammation model was reproduced by subplantar administration of 1% carrageenin solution in the amount of 0.05 ml/mouse (n=7). Anti-inflammatory effect of a single-use intravenous emulsion of the composition administered 15 minutes before induction of the carrageenin edema was evaluated. The control group included animals which were administered with a sterile saline solution according to the same procedure. Three hours after administration of anti-inflammatory agent, the animals were removed from the experiment by mortification, rear feet were amputated at a level of hip joints. Edema of feet was evaluated and influence of the liposomal compositions onto edema inhibition was calculated (% to the edema value in the control without treatment).

In all the described treatment schemes, the liposomal compositions of Examples 1-6 were used in the form of emulsion in the sterile 0.9% sodium chloride solution. In order to reconstitute the emulsion to the bottle with the lyophilized product stored at room temperature for 5 minutes, 18 ml of sodium chloride solution were added and stirred for 2 minutes.

In the treatment schemes, the administered dose of the product (mg/kg of body weight) was calculated according to the QC content with consideration of the QC/bottle content (Table 1).

Morphologic studies were conducted after subjecting the animals to euthanasia in the ARDS models under ether anesthesia in 24 hours after last administration of the liposomal composition. Samples of organs were fixed in neutral 10% formaline and placed into paraffin blocks according to standard methodology. Cut-offs were stained with hematoxylin-eosin and examined on a light microscope with photographic recording.

Experimental results were evaluated according to non-parametric statistic analysis methods using Statistica 5,5* package and Student's t-test (probability at value of p<0.05).

Table 3 provides evaluation of the anti-inflammatory activity of the liposomal QC compositions in the inflammation model.

TABLE 3

Pharmacological activity of the subject liposomal composition and the prototype composition regarding the anti-inflammatory effect in the inflammation model (anti-edema effect)

| Liposomal composition of example No. * | Edema degree in the inflammation model, c.u. | | Anti-inflammation effect-inhibition of edema **, % |
|---|---|---|---|
| | Control-without treatment | Influence of the liposomal composition | |
| 1 | 68.1 ± 0.3 | 38.4 ± 0.3 | 43.6 |
| 2: in the dose (according to QC content): | | | |
| 3.8 mg/kg | 72.0 ± 0.4 | 31.4 ± 0.4 | 55.0 |
| 5.7 mg/kg | 70.5 ± 0.3 | 22.1 ± 0.5 | 68.4 |
| 3 | 72.0 ± 0.3 | 41.0 ± 0.2 | 43.0 |
| 4 | 79.1 ± 0.4 | 47.6 ± 0.3 | 39.9 |
| 5 | 69.2 ± 0.5 | 32.4 ± 0.5 | 54.7 |
| 6-the prototype | 68.3 ± 0.3 | 42.1 ± 0.3 | 38.4 |

* Intravenous administration of the composition emulsion in the dose of 3.8 mg/kg according to the QC content
** Anti-inflammatory effect is determined according to % of the edema inhibition as compared to the control without treatment All the studied products exhibit valuable anti-inflammatory effect that is manifested as (38-55)% inhibition of the inducted edema. Embodiments of the subject invention has a higher pharmacological effect, namely, the examples 1-3 and 5 have a pharmacological effect degree which is 5-17% higher than the prototype composition (the difference is 1.4% in case of Example No. 4). It should be noted that the degree of the anti-inflammatory effect of the composition is positively dose-dependent (Table 3-dose-dependent increase to 68% for Example No. 2) which is important for explanation of schemes of the potential clinical use of the subject inventive product.

Tables 4 and 5 provide evaluation of the pharmacological activity of the subject liposomal composition and the prototype composition in ARDS according to parameters of the survival dynamics and body weight of the survived animals.

TABLE 4

Pharmacological activity of the subject liposomal composition and the prototype composition according to the parameter of the survival dynamics of the animals in ARDS in the HCl and LPS models according

| Liposomal composition ** according to the example and administration route*** | Number of animals survived within the group in the day after reproduction the of (survived/entered) ARDS model* | | | |
|---|---|---|---|---|
| | 1 | 2 | 4 | 6 |
| HCl model of ARDS | | | | |
| Example 1: | | | | |
| i/v | 7/7 | 6/7 | 6/7 | 5/7 |
| inh | 7/7 | 7/7 | 6/7 | 6/7 |
| i/v + inh | 7/7 | 7/7 | 7/7 | 7/7 |
| Example 2: | | | | |
| inh | 7/7 | 7/7 | 7/7 | 6/7 |
| i/v + inh | 7/7 | 7/7 | 7/7 | 7/7 |
| Example 4: | | | | |
| i/v | 6/7 | 5/7 | 5/7 | 5/7 |
| i/v + inh | 7/7 | 6/7 | 6/7 | 6/7 |
| Example 6-the prototype: | | | | |
| i/v | 6/7 | 5/7 | 5/7 | 5/7 |
| inh | 7/7 | 6/7 | 6/7 | 6/7 |
| i/v + inh | 7/7 | 7/7 | 6/7 | 6/7 |
| Control-pathology without treatment | 6/7 | 4/7 | 4/7 | 3/7 |
| LPS model of ARDS | | | | |
| Example 2: | | | | |
| inh | 7/7 | 6/7 | 5/7 | 5/7 |
| i/v + inh | 7/7 | 6/7 | 6/7 | 6/7 |
| Example 3: | | | | |
| i/v | 6/7 | 6/7 | 5/7 | 4/7 |
| i/v + inh | 6/7 | 6/7 | 6/7 | 5/7 |
| Example 4: | | | | |
| i/v | 6/7 | 5/7 | 5/7 | 4/7 |
| i/v + inh | 6/7 | 5/7 | 5/7 | 4/7 |
| Example 5: | | | | |
| inh | 7/7 | 6/7 | 5/7 | 5/7 |
| i/v + inh | 7/7 | 6/7 | 6/7 | 6/7 |

TABLE 4-continued

Pharmacological activity of the subject liposomal composition and the
prototype composition according to the parameter of the survival dynamics
of the animals in ARDS in the HCl and LPS models according

| Liposomal composition ** according to the example and administration route*** | Number of animals survived within the group in the day after reproduction the of (survived/entered) ARDS model* | | | |
|---|---|---|---|---|
| | 1 | 2 | 4 | 6 |
| Example 6-the prototype: | | | | |
| i/v | 6/7 | 5/7 | 5/7 | 4/7 |
| inh | 6/7 | 4/7 | 4/7 | 4/7 |
| i/v + inh | 6/7 | 6/7 | 5/7 | 5/7 |
| Control-pathology without treatment | 5/7 | 3/7 | 2/7 | 2/7 |

*Initial number of animals in each group n = 7.
** Dose of liposomal composition according to the examples is 3.8 mg/kg of body weight according to QC content
***Administration route: i/v - intravenous; inh - inhalation; i/v+inh - combined intravenous and inhalation administration

TABLE 5

Pharmacological activity of the subject liposomal composition and the
prototype composition according to the influence onto the body weight
parameter of the animals in ARDS in the HCl model

| Liposomal composition ** according to the example and administration route*** | Initial weight of the animals*, g (±0.5) | Mass of the animals after reproduction of the ARDS model*, g (±0.7)/% to the initial weight per day: | |
|---|---|---|---|
| | | 3rd | 6th |
| Example 1: | | | |
| i/v | 24.7 | 23.3/−7.5 | 23.3/−6.5 |
| inh | 24.9 | 23.5/−7.0 | 23.4/−6.0 |
| i/v + inh | 24.6 | 23.7/−6.0 | 23.2/−5.4 |
| Example 2: | | | |
| inh | 25.6 | 23.9/−6.8 | 24.9/−5.1 |
| i/v + inh | 24.9 | 23.5/−5.8 | 24.2/−4.7 |
| Example 4: | | | |
| i/v | 25.6 | 23.4/−8.6 | 23.5/−8.3 |
| i/v + inh | 24.9 | 23.3/−6.3 | 23.5/−6.0 |
| Example 6-the prototype: | | | |
| i/v | 26.0 | 23.7/−8.9 | 23.8/−8.5 |
| inh | 25.8 | 24.0/−7.3 | 24.4/−6.6 |
| i/v + inh | 25.9 | 24.0/−6.6 | 24.7/−5.8 |
| Control-pathology without treatment | 25.0 | 22.4/−10.2 | 22.0/−12.0 |
| Control-intact animals | 25.4 | 26.2/+3.2 | 27.0/+6.3 |

*Initial weight (before reproduction of the model) determined in the groups of 7 animals; the weight is determined in next days for the survived animals.
** Dose of liposomal composition according to the examples is 3.8 mg/kg of body weight according to QC content
***Administration route: i/v-intravenous; inh-inhalation; i/v + inh-combined intravenous and inhalation administration ARDS in the HCl model resulted in death of the animals on the first and second days after acidic aspiration (1 of 7 and 3 of 7 animals respectively). In day 6 of follow-up, the survival rate was 43% of the population. Development of ARDS was accompanied by a characteristic clinical performance with depression of respiration cycle and depth, reduction of motor performance and ptosis, reduction of food and water consumption. In day 6 after pathology modeling, recovery of clinical state of the animals was not observed.

The studied liposomal compositions possess significant pharmacological activity in the HCl model of ARDS, and the composition of Examples Nos. 1 and 2 exhibited advantages as compared to the prototype composition: it increased survival rate in day 1, 2 and 4, provided 100% prevention of animals' death in day 6 of follow-up (as compared to 85% for the prototype). Therewith, the clinical condition of the animals (respiration, motor performance etc.) was increased after day 2 and recovered on day 6 of follow-up, while the prototype composition did not provide full normalization of the clinical performance. Opportunely it should be noted that the composition of Example No. 4 has only minor advantages in terms of survival rate dynamics as compared to the prototype.

In the LPS model of ARDS, death of the control animals without treatment was permanently increased from 29% to 71% from the first day until the sixth day of follow-up.

Generally, the clinical condition of the population was close to the clinical performance in the HCl model of ARDS, but it was characterized by a rather sharper complication of respiration, drop of motor performance and convulsive reactions, while all negative manifestations in the animals which survived in the follow-up dynamics were enhanced.

Pharmacological effect of the studied liposomal compositions in the LPS model of ARDS manifests as a clear protective effect for animals' lives. The liposomal products ensure survival rate of animals being 85-100% and 57-85% in the first day and sixth day of follow-up. Therewith, the positive effect of the subject embodiments of Examples Nos. 2, 3 and 5 onto the survival rate in each day is 15% greater than the one of the prototype composition (29% for the Examples Nos. 2 and 5 at the end of testing). It should be noted that there was a relief of pathological clinical symptoms in the animals survived after the treatment: recovery of respiration, motor performance and coordination, and, at the same time, reduction of duration of the convulsive reactions (they are almost absent as a result of the effect of the claimed compositions of Examples Nos. 2 and 5).

Pharmacological activity of the liposomal products in ARDS (in case of significant reduction of food and water consumption being a part of the pathological clinical performance) is characterized by their positive effect onto the body weight dynamics. In order to provide proper evaluation of the body weight, the HCl model was used, where the pharmacological effect of the compositions at the end of the follow-up period caused 100% survival rate of the animals as compared to 29% in the LPS model. In ARDS without treatment reduction of the body weight of 10.2% and 12.0% respectively in days 3 and 6 was observed (Table 5), while a natural body weight gain of intact animals over time was present. Owing to the therapeutic effect of the liposomal products, the permanent reduction of the weight in the same time periods was only (6.0-8.9)% and (4.7-8.5)%, respectively. Stable positive effect of the claimed composition relative to the recovery of the body weight is 0.5-3.4% better as compared to the one of the prototype (for the Examples Nos. 1 and 2), although for the Example No. 4 the insignificant advantages appear as a trend only.

It should be noted that according to the task of the invention, the pharmacological activity of the subject liposomal compositions was confirmed during treatment of the ARDS at all used treatment schemes, and a comparatively higher effect was achieved in case of combination of the intravenous and inhalation administration of the product. Formally, this phenomenon was not expected, since the used algorithm of the combined administration did not imply only formal combination of two separate administration schemes.

Owing to reproduction of the alternative HCl and LPS models, characteristic morphological manifestations of ARDS being a severe inflammatory pulmonary affection were verified, as well as the pharmacotherapeutic effect of the liposomal compositions was confirmed for the influence onto histomorphological features of ARDS which are visualized and described in the drawings.

BRIEF DESCRIPTION OF THE FIGURES

FIG. 1(a)—edema of peribronchial and perivascular connective tissue of lungs with lymphocytic infiltration;
FIG. 1(b)—locus of hyperplasia and metaplasia of epithelium of mucosal lining of bronchus.

FIG. 2(a)—subendothelial edema of pulmonary artery, thickening and ribbed surface of its internal membrane, edema of smooth muscle fibers;
FIG. 2(b)—locus of emphysema at a periphery of a pulmonary lobule.

FIG. 5(a) and
FIG. 5(b)—individual locuses of peribronchial infiltration with mononuclear cells. Expanded lumens of bronchia and small bronchiectasia having cavities which are filled with mucin.

FIG. 6(a)—infiltration of walls of terminal bronchias, alveolar ducts and saccules with mononuclear cells;
FIG. 6(b)—inflammatory changes of epithelium of the mucosal lining of bronchus.

FIG. 7(a)—treatment with intravenous administration of the liposomal composition of Example 2, moderate edema and infiltration of interalveolar septums with lymphocytes and macrophagocytes.
FIG. 7(b)—treatment with intravenous administration of the liposomal composition of the Example 6 being the prototype, small locuses of the lymphocytic infiltration at the periphery of bronchus with expanded lumens and vessels having a moderate blood filling.

FIG. 8(a)—moderate infiltration of interalveolar septums in the lungs with lymphocytes and macrophagocytes;
FIG. 8(b)—apparent vacuolization of cytoplasm.

FIG. 9(a)—moderate capillary plethora;
FIG. 9(b)—moderate infiltration of perivascular connective tissue with macrophagocytes without any essential features of dystrophy in cardiac myocytes.

Development of ARDS in the HCl model manifests in lungs and bronchus with morphological features which are characteristic for the inflammation: apparent pulmonary plethora with alteration of a wall of vessels, inflammatory changes of pulmonary interstitium and parenchyma (sometimes in a form of purulent bronchitis forming abscess pneumonia), manifestations of bronchiolitis and ventilation-perfusion imbalances (FIGS. 1(a)-2(b)).

Figure 1A:
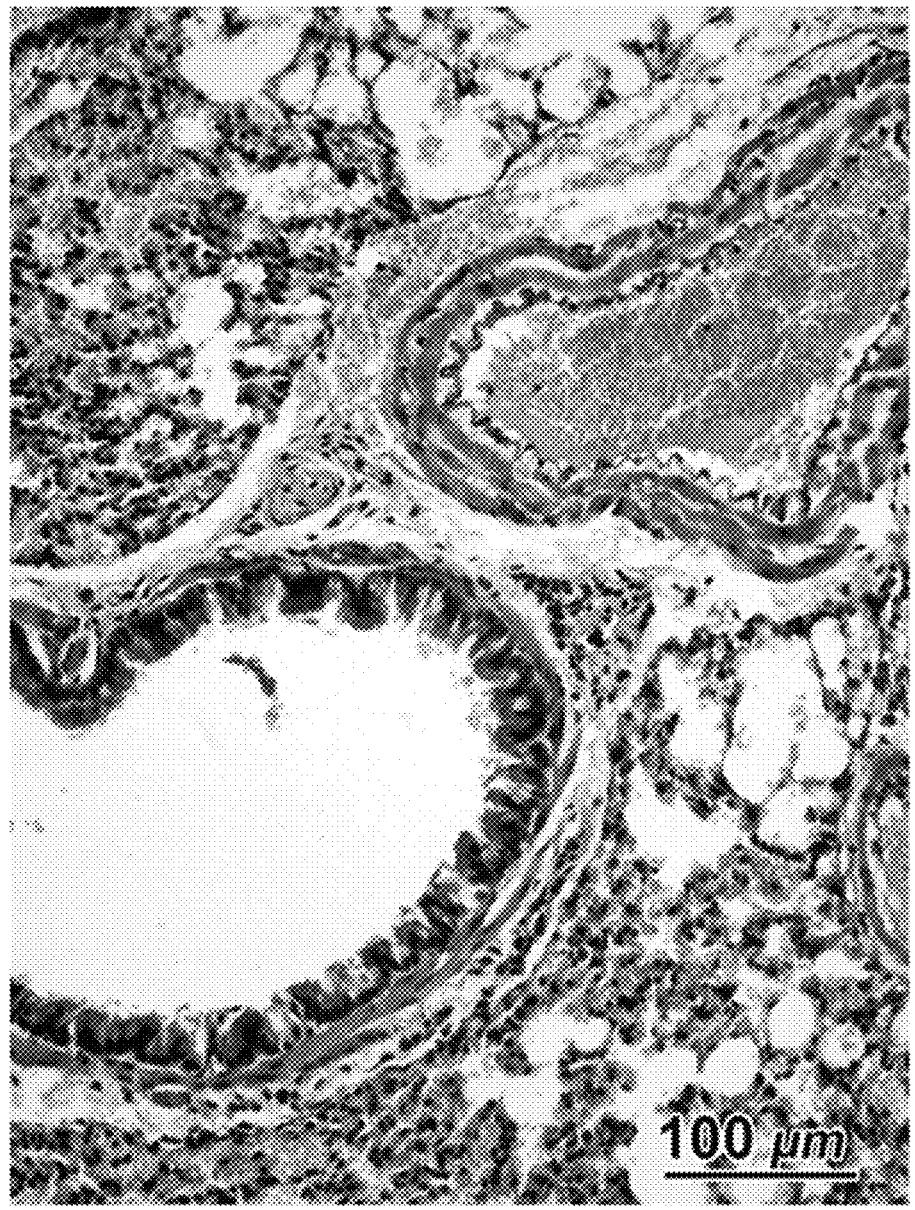
FIGS. 1(a) and 1(b)—HCl model of ARDS. Animals which survived on day 6, namely.
Figure 1B:
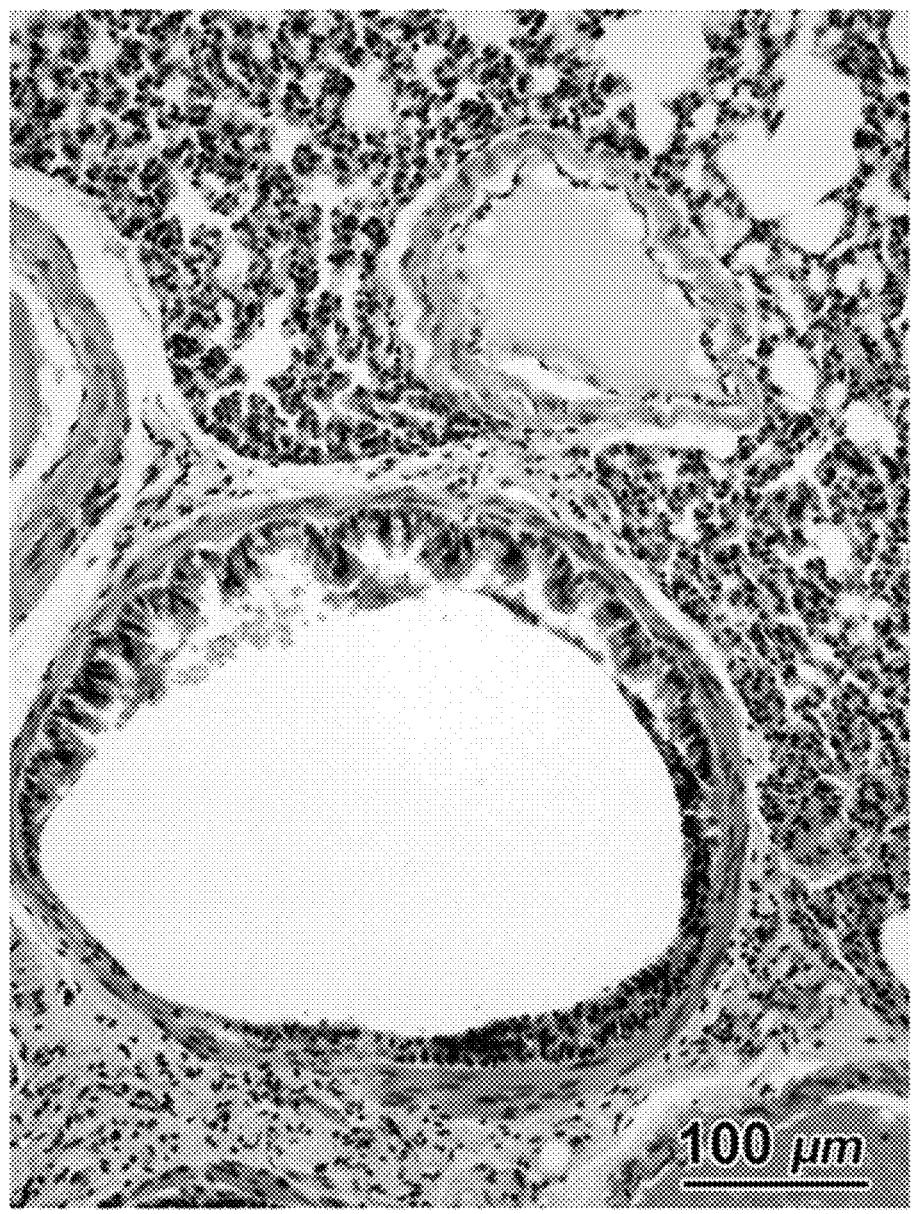
Figure 2A:
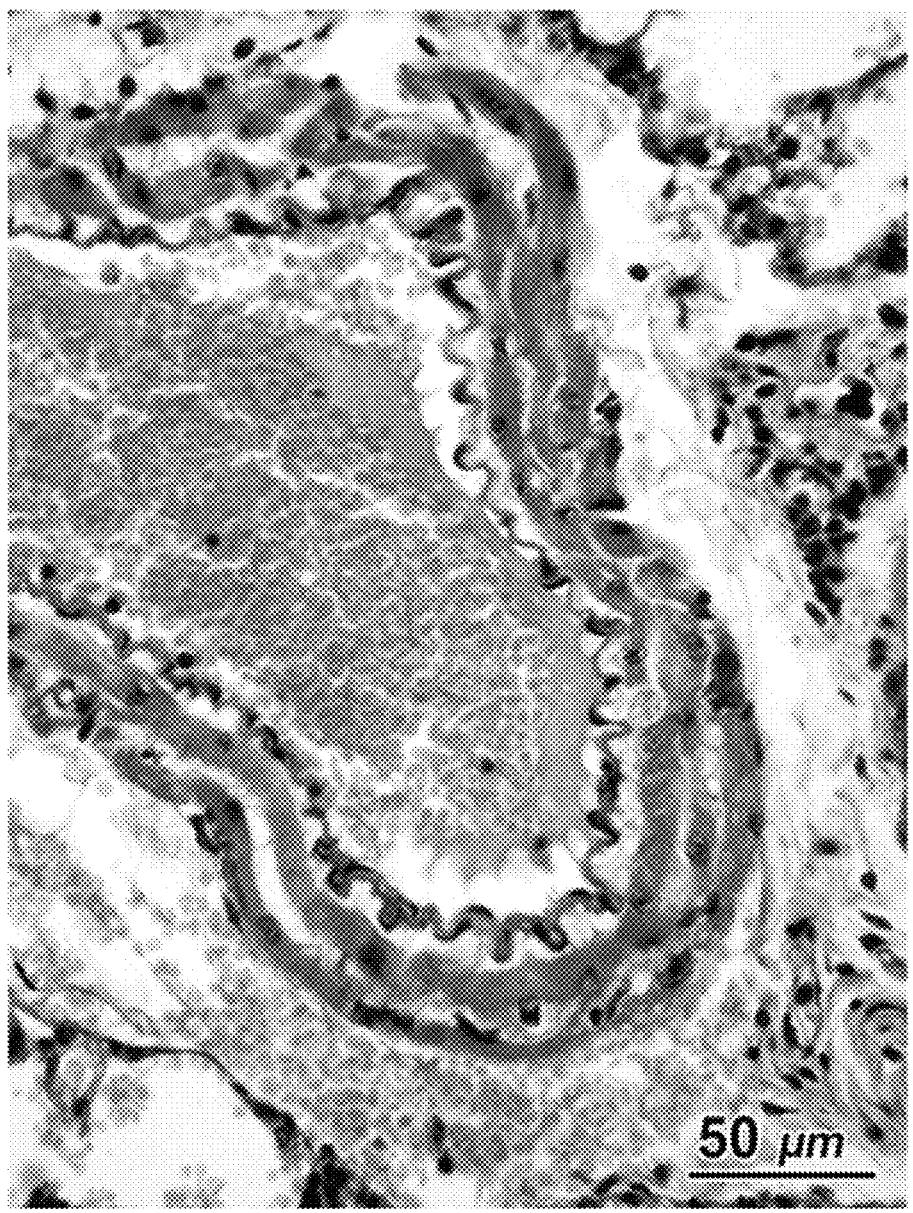
FIGS. 2(a) and 2(b)—HCl model of ARDS. Animals which survived on day 6, namely.
Figure 2B:
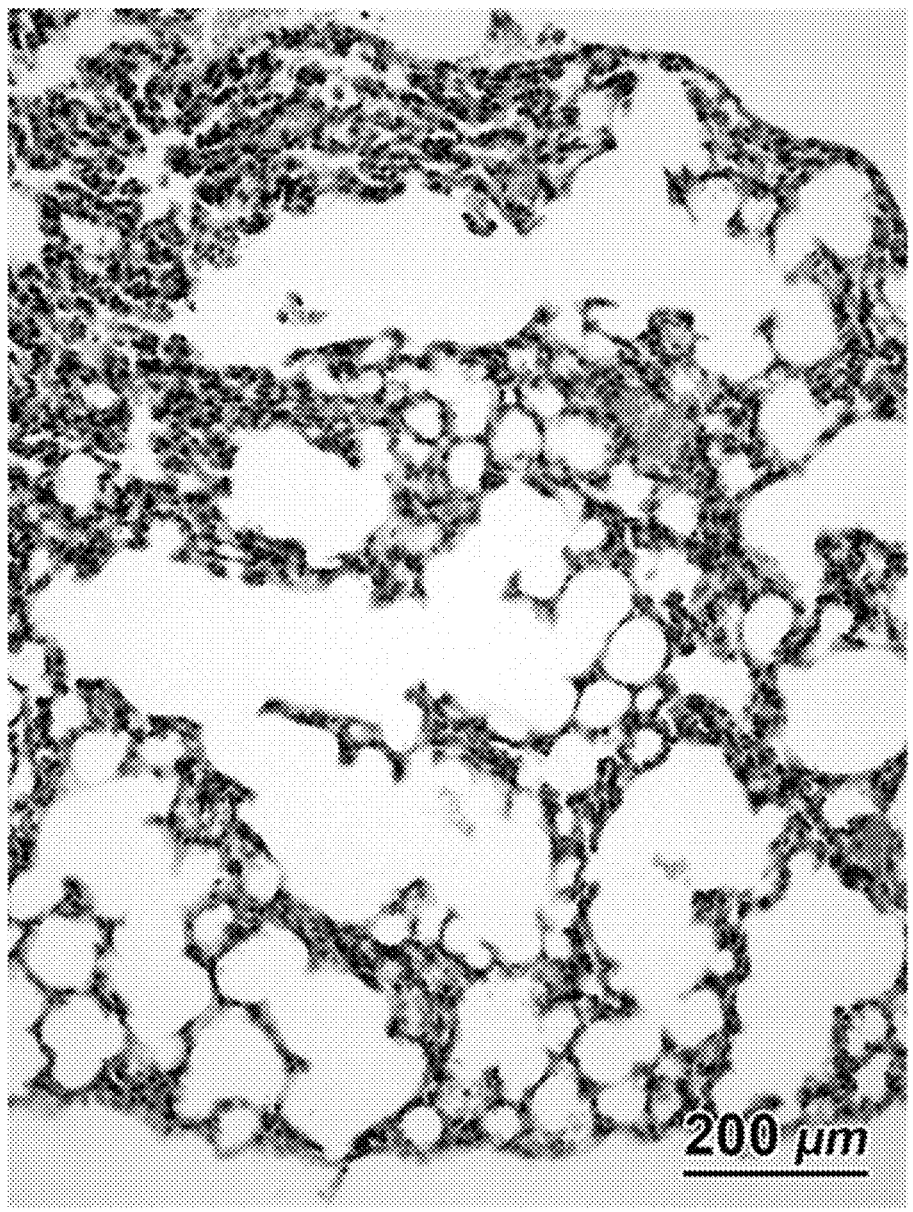
Figure 3:
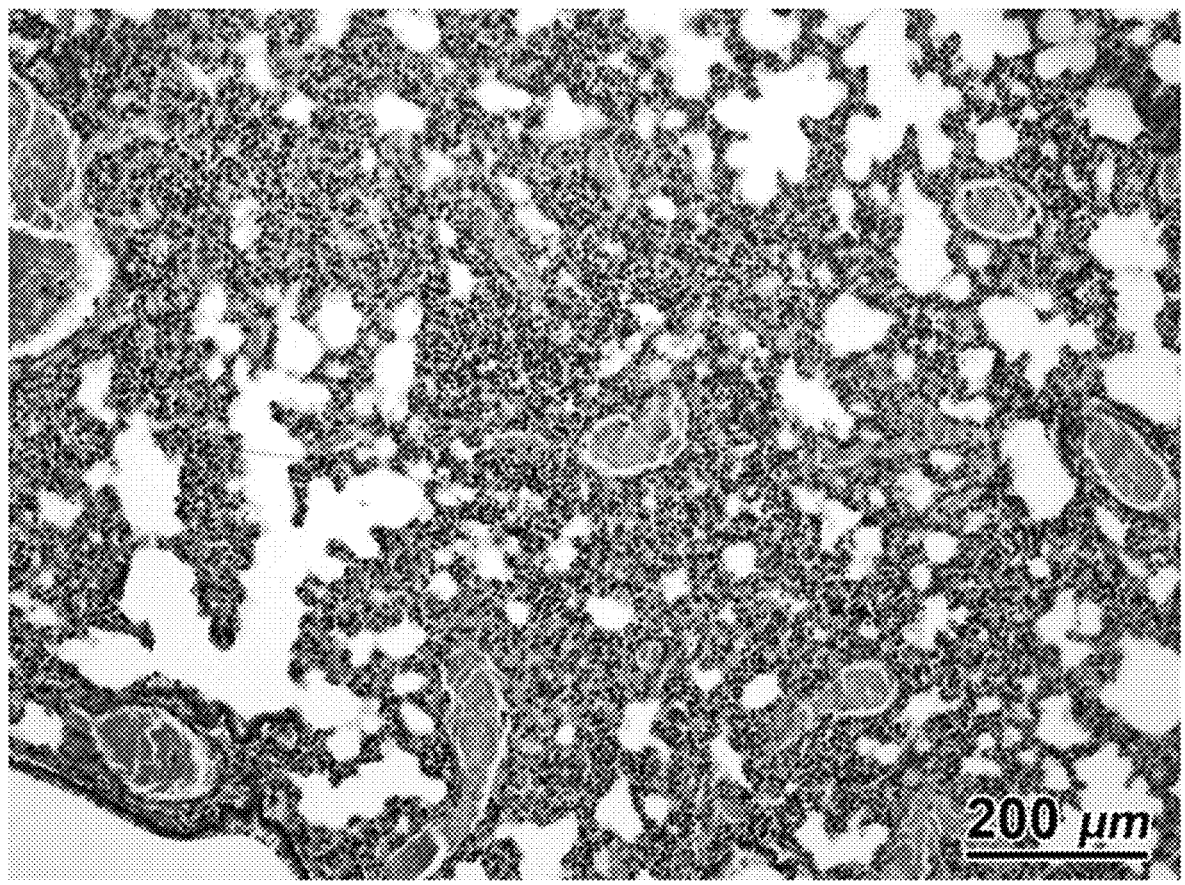
FIG. 3—LPS model of ARDS. Animals which died on day 6. Interstitial hemorrhagic pneumonia. Apparent venous plethora of lungs and ventilation-perfusion imbalances.
Figure 4:
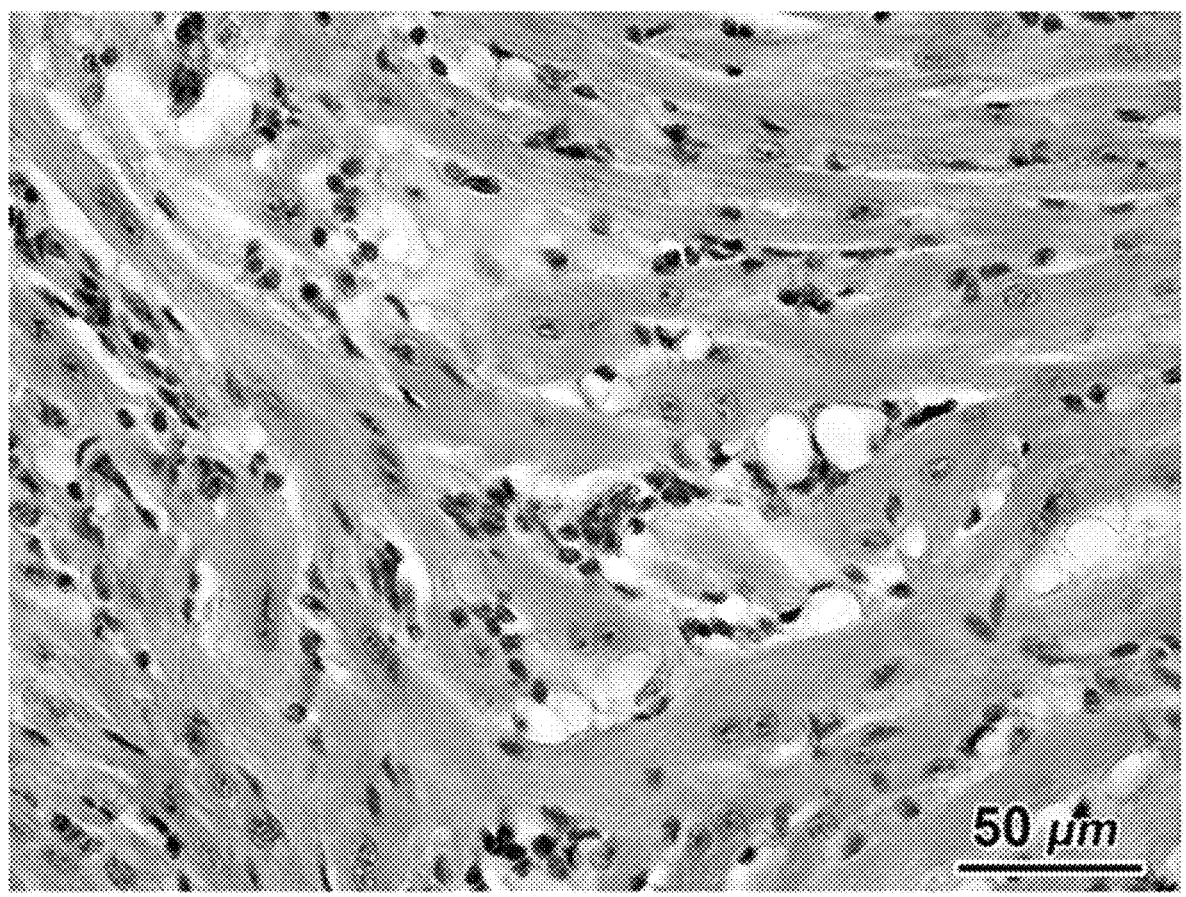
FIG. 4—LPS model of ARDS. Animals which survived on day 6. Left ventricle of myocardium—apparent infiltration of perivascular connective tissue by lymphocytes and macrophagocytes. Dystrophic changes of cardiac myocytes.
Figure 5A:
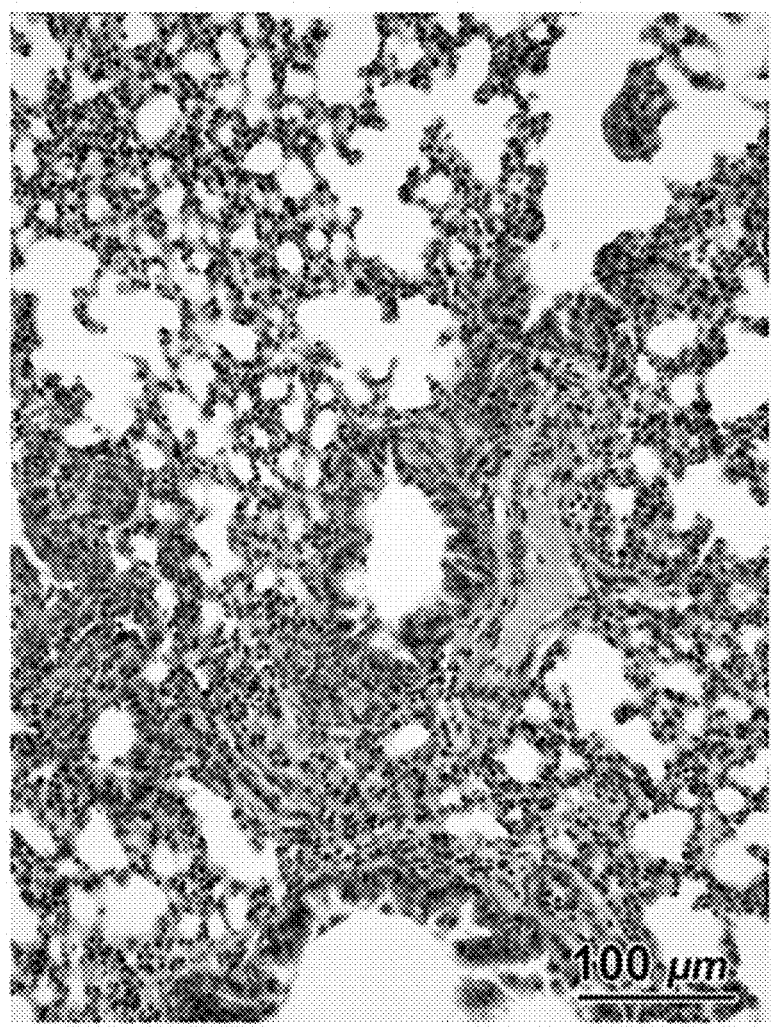
FIGS. 5(a) and 5(b)—HCl model of ARDS. Animals which survived on day 6. Combined inhalation and intravenous administration of the liposomal composition of Example 1, namely.
Figure 5B:
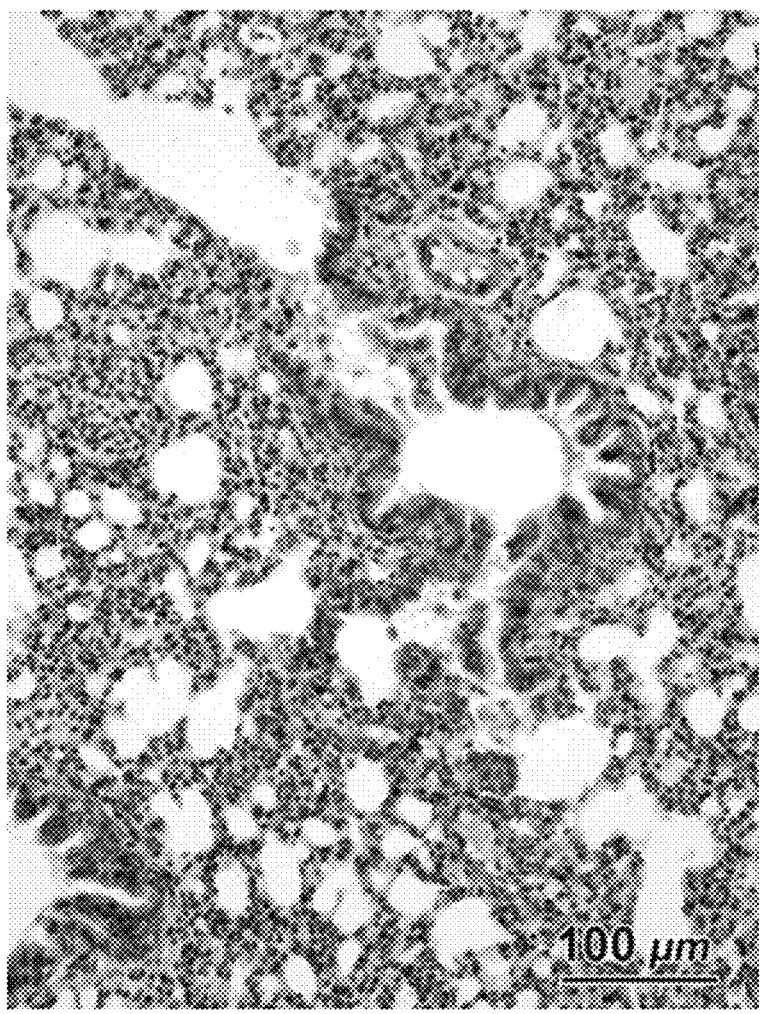
Figure 6A:
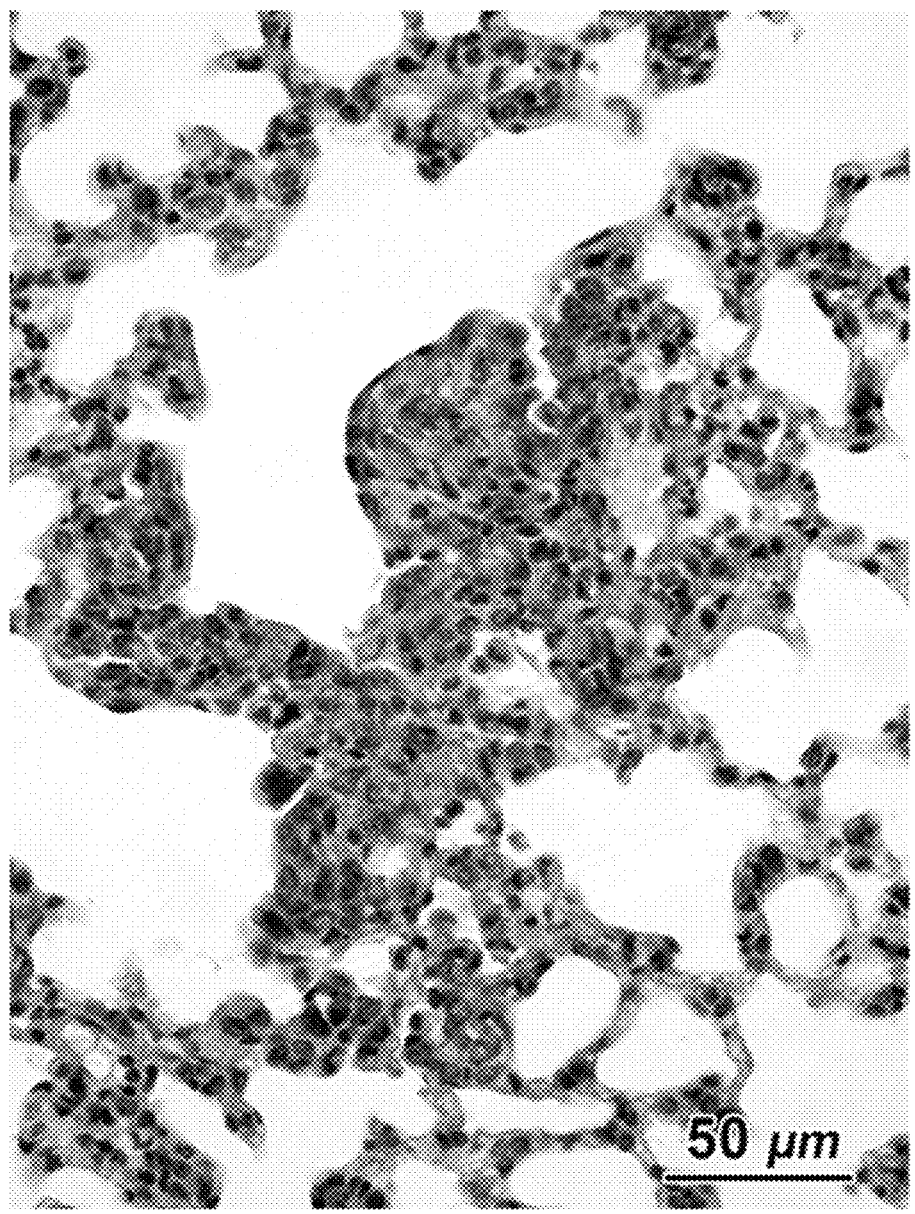
FIGS. 6(a) and 6(b)—HCl model of ARDS. Animals which survived on day 6. Combined inhalation and intravenous administration of the liposomal composition of Example 6 (the prototype), namely.
Figure 6B:
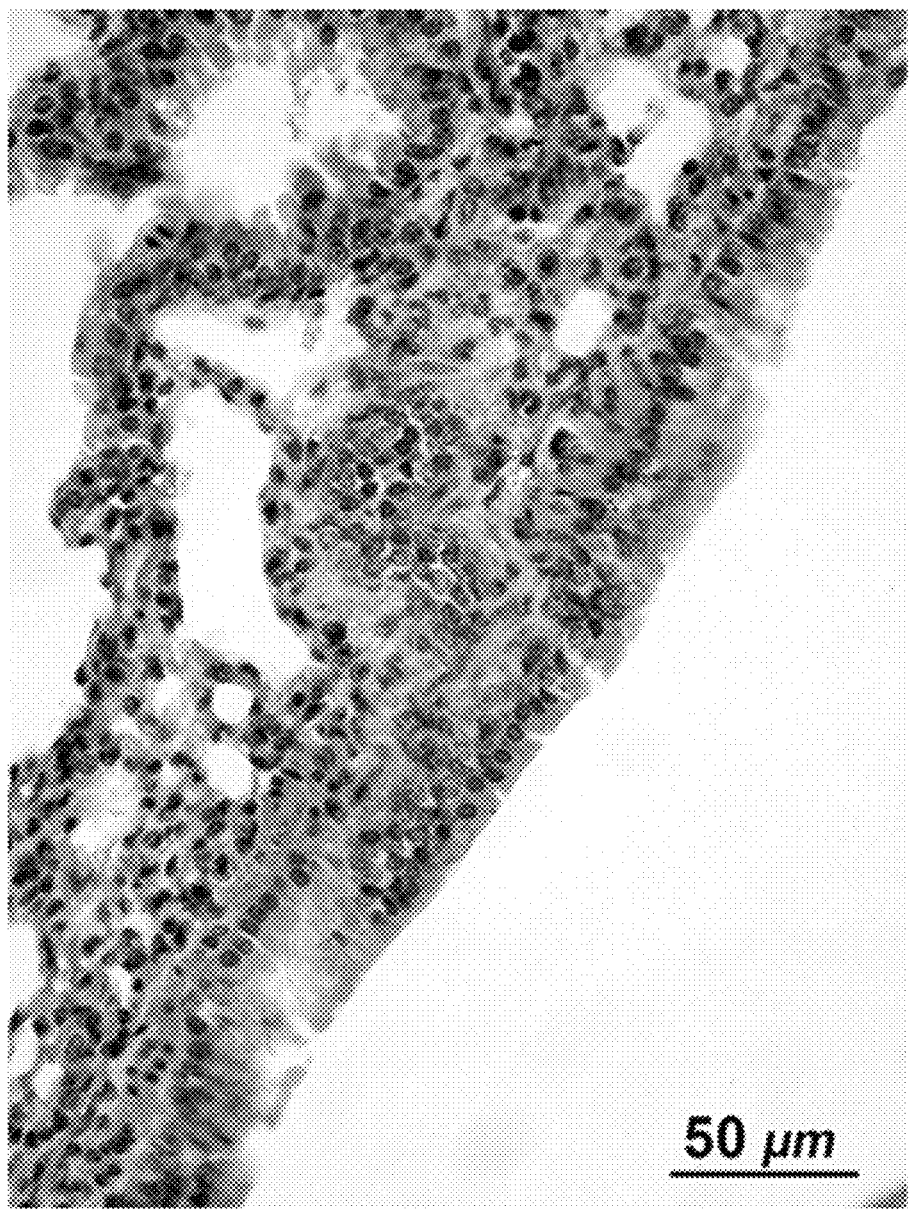
Figure 7A:
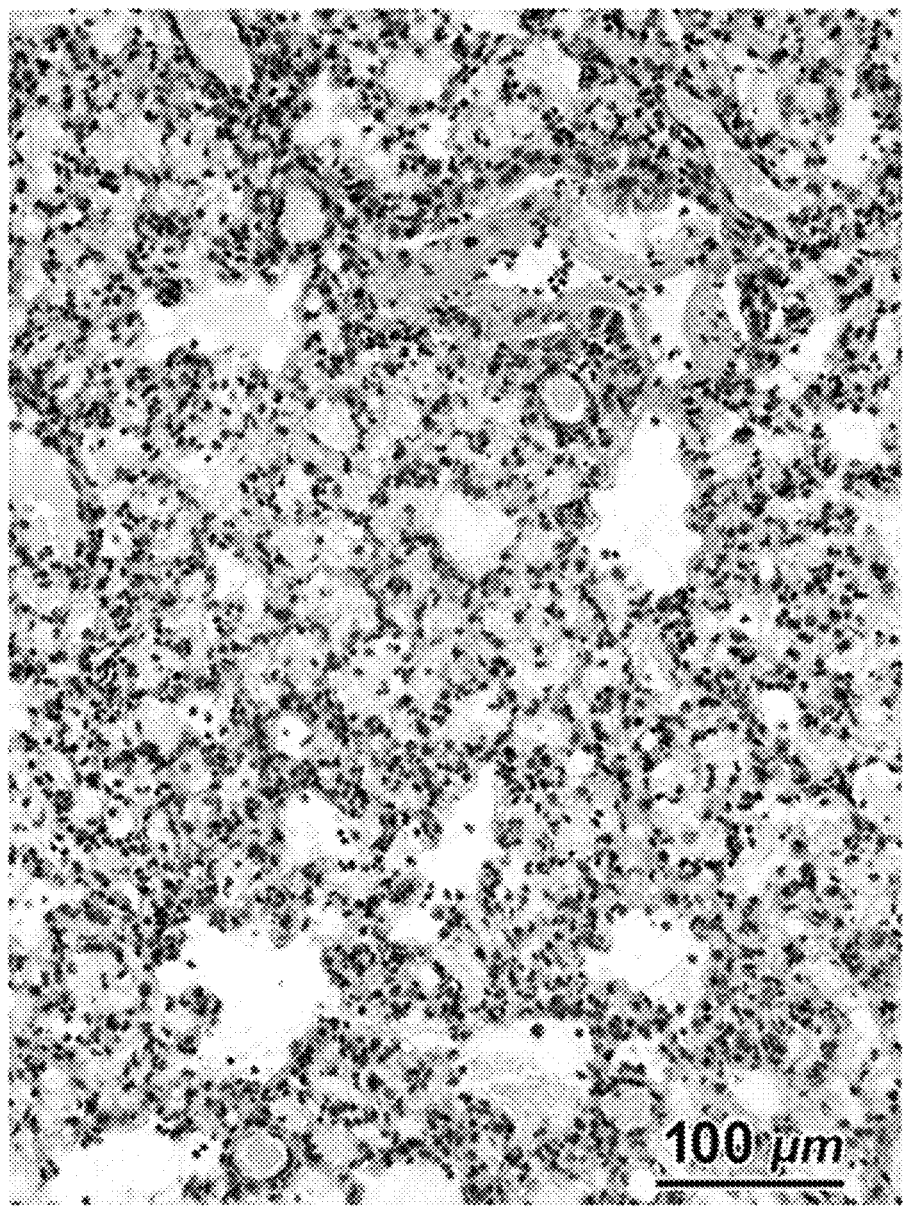
FIGS. 7(a) and 7(b)—LPS model of ARDS. Animals which survived on day 6, namely.
Figure 7B:
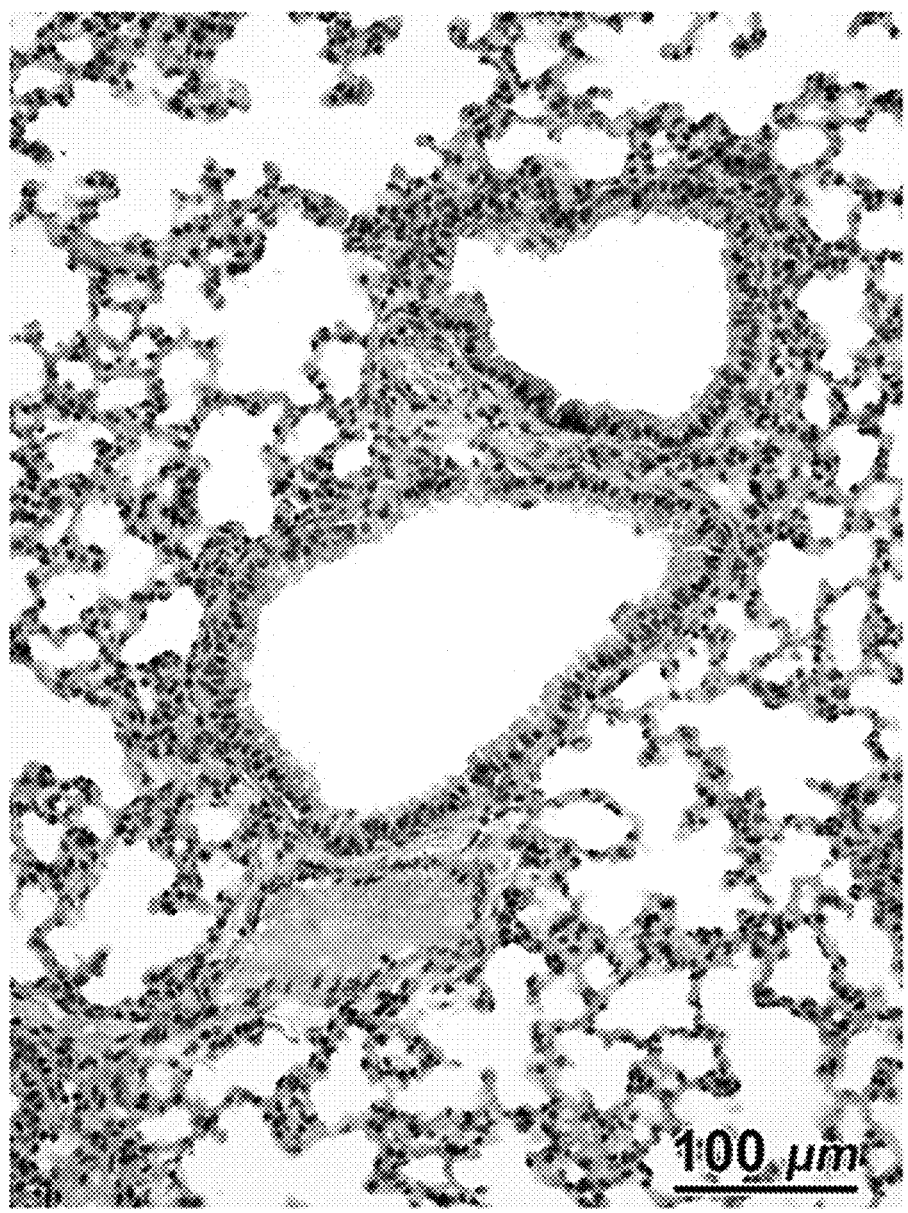
Figure 8A:
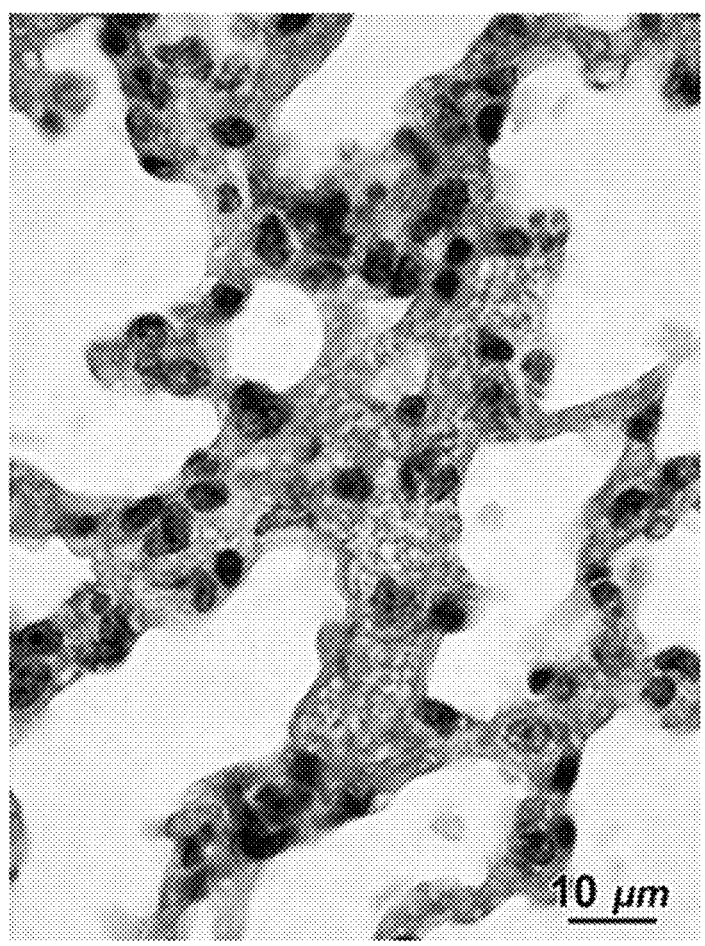
FIGS. 8(a) and 8(b)—LPS model of ARDS. Animals which survived on day 6. Treatment with combined inhalation and intravenous administration of the liposomal composition of Example 3, namely.
Figure 8B:
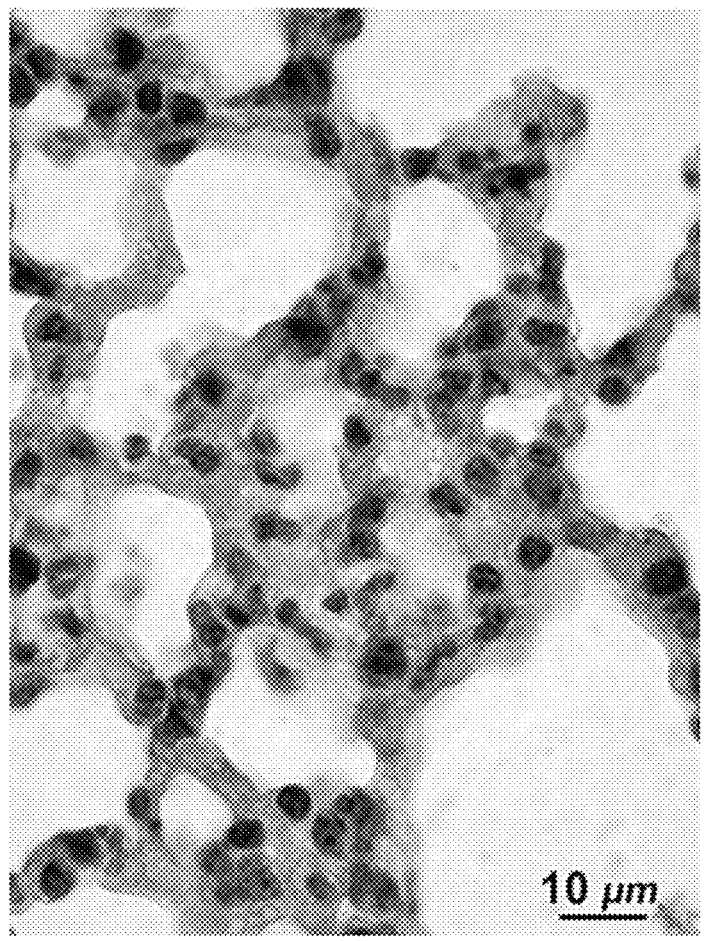

Apparent deep structural damages of respiratory organs as a result of "fatal" LPS model of ARDS are reliably manifested as an apparent vascular reaction with development of interstitial hemorrhagic pneumonia associated with apparent pulmonary plethora and ventilation-perfusion imbalances, as well as damage of vascular wall (FIG. 3). Apparent capillary plethora is noted in the left ventricle of myocardium that is accompanied by infiltration of the tissue with lymphocytes and dystrophic changes of individual cardiac myocytes (FIG. 4). Such histological features of myocardium correspond to inflammatory changes of a systemic nature.

Pharmacological activity of the studied liposomal compositions is manifested with a therapeutic and prevention influence onto morphology of target organs affected by ARDS. Manifestations of the effect of the liposomal products principally coincide in both alternative ARDS models, but they are the most obvious in the "fatal" LPS model at combined inhalation and injection administration of the composition that results in three-time increase of the survival rate of the animals (Table 4).

Figure 9A:
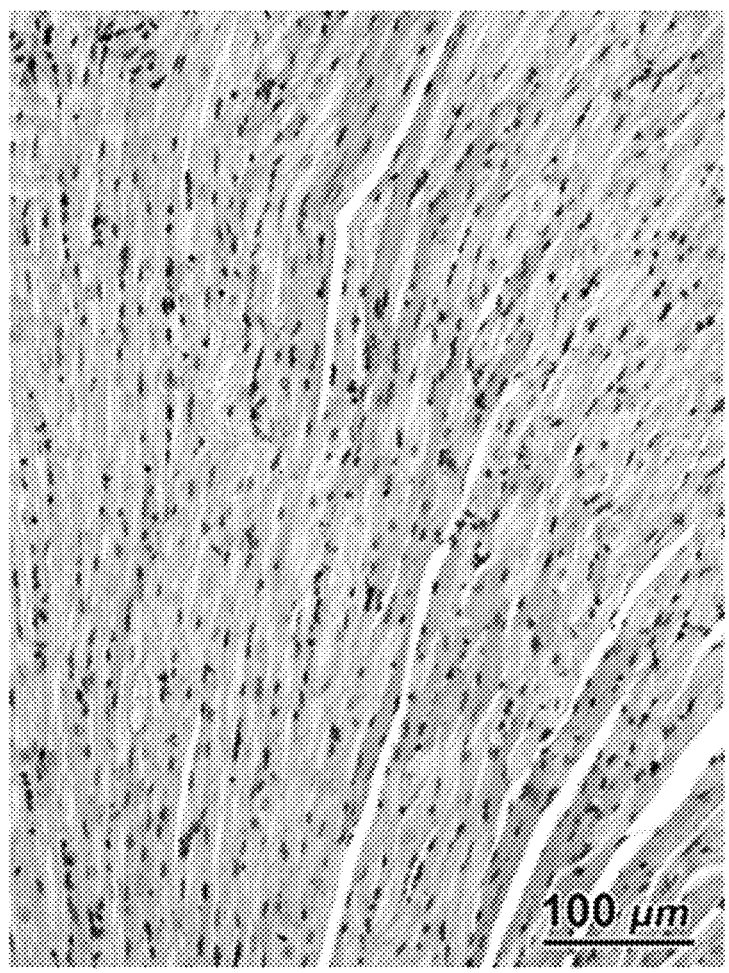
FIGS. 9(a) and 9(b)—LPS model of ARDS. Animals which survived on day 6. Treatment with combined inhalation and intravenous administration of the liposomal composition of Example 2. Left ventricle of myocardium, namely.
Figure 9B:
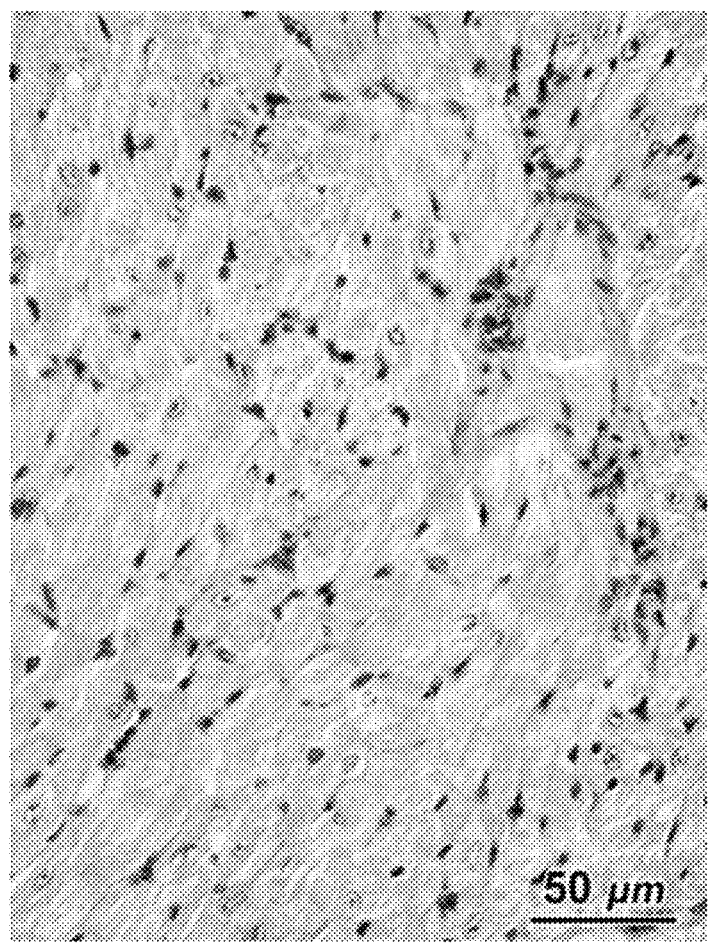

Generally, the treatment effect of the subject liposomal compositions is manifested by a significant reduction of pathological morphological changes in lungs and bronchus (FIGS. 5-8(b)): enhancement of resistance of walls of blood vessels and mucosal lining of bronchus; reduction of inflammatory changes of the pulmonary interstitium and parenchyma, as well as absence of abscesses and abscess pneumonia. Administration of the composition protects terminal bronchias and alveolas of structures of respiratory system, thereby inhibiting development of ventilation-perfusion imbalances as a mechanism of ARDS development. Moderate capillary plethora is noted in the left ventricle of myocardium only in individual cases (FIGS. 9(a) and 9(b)).

Activity of the prototype composition relative to recovery of the morphological structure of the affected organs is close in terms of manifestations, but is inferior in terms of influence degree as compared to the liposomal product: focal lymphocytic infiltration is still present at the periphery of bronchus and vessels moderately filled with blood, which is accompanied by vacuolization of cytoplasm in the alveolas of macrophagocytes (FIGS. 6(a)-7(b)), as well as dystrophic changes of cardiac myocytes of the left ventricle of cardiac myocardium.

Results of comparison of the pharmacological activity in terms of parameters of the anti-inflammatory effect and therapeutic effect in the alternative ARDS models prove the high pharmacological quality of the subject liposomal compositions of QC and zinc having provably identified formulation at different parenteral routes of administration to the body.

The integrally highest pharmacological activity and optimal pharmaceutical characteristics are peculiar to the liposomal compositions of the Examples 1-3, wherein the mass ratio of components QC:PC:lactose:zinc is 1:36.7:54.5:0.11-0.43. Deviations from said formulation by excluding zinc in the prototype or by relative reduction of its content in Example 4 (the corresponding mass ratio is 1:36.7:54.5:0.06) result in a relative drop of the pharmacological activity of the composition. This conclusion is the most obvious for the prototype composition which provides no presence of zinc. For the liposomal composition having the mass ratio QC:PC:lactose:zinc of 1:36.7:54.5:0.89 (Example 5), i.e., having the increased zinc content, the high pharmacological activity is accompanied by certain precautions as to the pharmaceutical quality (presence of precipitate and signs of emulsion oxidation), thereby deteriorating a forecast of its safe application and stability.

Optimal combination of the pharmacological effect in terms of therapeutic effect in ARDS, anti-inflammatory effect and safety with data of the positive pharmaceutical identification proves advantages of the subject liposomal composition of QC and zinc as compared to the liposomal product of QC according to the prototype when solving the problem of provision of the liposomal agent having a high pharmacological activity at different parenteral routes of administration to the body.

The stated information justifies the expediency of the proposed liposomal composition of quercetin and zinc as effective safe pharmacotherapeutic agent in acute respiratory distress syndrome.

SOURCES OF INFORMATION

1 Feldman C., Shaddock E. Epidemiology of lower respiratory tract infections in adults//Expert Review of Respiratory Medicine 2019, 13:1, 63-77.
2 Paul Glezen W., Floyd W. Denny. Epidemiology of Acute Lower Respiratory Disease in Children//N Engl J Med 1973; 288:498-505. doi: 10.1056/NEJM197303082881005
3 Rom W N, Bitterman P B, Rennard S I, Cantin A, Crystal R G. Characterization of the lower respiratory tract inflammation of nonsmoking individuals with interstitial lung disease associated with chronic inhalation of inorganic dusts//Am Rev Respir Dis. 1987 December-136(6): 1429-34.
4 Meger N. I., Gattinoni L., Calfee C. S. SEMINAR. Acute Respiratory distress syndrome//The Lancet V. 398, P 622-637, Aug. 14, 2021. doi.org/10/1016/S0140-6736 (21)00439-6.
5 Miller K. Acute Respiratory distress syndrome/ WebMD. —December 2021.
6 A vicious circle between oxidative stress and cytokine storm in acute respiratory distress syndrome pathogenesis/G. H. Meftahi, Z. Bahari, Z. Jangravi, M. Iman// Ukr.Biochem.J. 2021; Volume 93, Issue 1. P 18-29 doi: https://doi.org/10.15407/ubj93.01.018
7 COVID-19 cytokine storm: The anger of inflammation/M. Mahmudpour, J. Roozbeh; M. Keshavarz et al.//Cytokine; 133: 155151, 2020 09. |MEDLINE|ID: —437203
8 Empson S., Rogers A. J., Wilson J. G. Acute Respiratory distress syndrome COVID-19//*Crit Care Clin.* 2022 July; 38(3): 505-519. NLM database. Published online 2022 Feb. 28. doi: 10.1016/j.ccc.2022.02.001/
9 Asymtomatic carrier state, acute respiratory disease, and pneumonia due to severe acute respiratory syndrome coronavirus/Cheng-Ch. Lai, Yen-H. Liu, Cheng-Y. Wang at al.//J. Microbiol. Immun. and Infection, V. 33, 2020, pp. 404-412.
10 Nat. Heart, Lung and Blood Institute/An Office. Website of US government. Health Topics. This is an informational and educational material that cannot be printed. The specific file is: www.nhlbi.nih.gov/health/ards. The file provides information on various aspects of distress syndrome. The reader chooses the area of interest.
11 Flavonoids: a review of probable mechanisms of action and potential applications/Nijveldt R J, van Nood E, van Hoorn D E et al.//Am. J. Clin Nutr. 2001 October, 74(4): 418-25.
12 M. A. Read. Flavonoids: Naturally occurring anti-inflammatory agents//Am. J. Pathol. 1995, V. 147. —pp. 235-237.

13 Bishoff S C. Quercetin: potentials in the prevention and therapy of diseases/Curr. Opin. Clib. Nutr. Metab. Cure. —2008. —V. 11, N 6, pp. 733-740.

14 Ganesan, S., Faris, A. N., Comstock, A. T. et al. Quercetin inhibits rhinovirus replication in vitro and in vivo/Antiviral Research 2012, N 94(3). —p. 258-271.

15 Quercetin and vitamine C: An experimental, synergistic therapy for prevention and treatment of SARS-COV-2 related disease (COVID-19)/R. M. Biancatelli, M. Berilli, J. D. Catravas, P. Marik/Frontiers in Immun. —2020, V.11, art. 1451, p. 1-10.

16 Quercetinum: instruction, analogues/https://compendium.com.ua.

17 Drug delivery systems: An updated review//G. Tiwari, R. Tiwari, B. Sriwastawa et al/Int J Pharm Investig. —2012 January-March; 2(1): 2-11. doi: 10.4103/2230-973X.96920

18 Declarative patent for invention UA 38504 A, IPC A61K 9/14, A61K 31/79, A61K31/455, publ. on May 15, 2001.

19 Patent for invention RU 2181051, IPC A61K 33/22, A61K 9/08, A61K 31 351, A61K 31/198, publ. on Apr. 10, 2002.

20 Application WO2011019677 A1, IPC (2006.01): A23L 1/00, A23L 1/30, publ. on Feb. 17, 2011.

21 Synthesis of Quercetin-Metal Complexes, In Vitro and In Silico Anticholinesterase and Antioxidant Evaluation, and In Vivo Toxicological and Anxiolitic Activities/W. da Silva, S. de Oliveira Pinheiro, D. Alves et al//Neurotox Res. 2020 April; 37(4):893-903.doi: 10.1007/s12640-019-00142-7.

22 Synthesis, characterization, and pharmacological evaluation of some metal complexes of quercetin as P-gp inhibitors/K. Shastrala, S. Kalam, K. Damerakonda et al//Future Journal of Pharmaceutical Sciences. —volume 7, Article number: 99 (2021).

23 A simple liposome assay for the screening of zinc ionophore activity of polyphenols./G. Clergeaud, H. Dabbagh-Bazarbachi, M. Ortiz et al//Food Chemistry Volume 197, Part A, 15 Apr. 2016, Pages 916-923.

24 Pracad A S. Discovery of zinc for human health and biomarkers of zinc deficiency./In: Molecular, genetic and nutritional aspects of trace minerals.//Acad. Press, Cambridge, 2017. —pp. 241-260.

25 Zinc-quercetin complex: From determination to bioactivity/S Uskoković-Marković, M. Milenković, L. A. Pavun//Acta agriculturae Serbica 2015, 25(50): 113-120, DOI:10.5937/A ASer 2050113U.

26 Compendium. Drugs. Corvitin®. Instruction. https://compendium.com.ua

27 Pharmaceutical and Biomedical Aspects of Drugs/Edited by I. M. Pertsev-Vinnytsia, 2007. Only the Title and Table of Contents are provided. The reference is to Chapter 7, Section 7.2.4. Excipients.

28 Elsevier B. V. Polyvinylpyrrolidone. ScienceDirect. 2020. Reproduced from: sciencedirect.com. An article from sciencedirect.com—Journal of Drug Delivery Science and Technology: M. Kurakula, K. Pharmaceutical assessment of polyvinylpyrrolidone (PVP): As excipient from conventional to controlled delivery systems with a spotlight on COVID-19 inhibition 29 The State Pharmacopoeia of Ukraine, 2015: Liposomal medicinal products N: pages 1036-1038.

30 Priprem A., Watanatorn J., Sutthiparinyanout S., Phachonpai W. Anxiety and cognitive effects of Quer liposomes//Nanomedicine: Nanotechn. Biol. And Medic. —2008. —Vol. 4, N 1. pp. 70-78.

31 Patent CN 100367968 C, IPC: A61K 31/352; A61K 47/34; A61K 9/127; A61K 9/14; A61P 29/00; A61P 35/00; A61P 39/06; A61P 9/10, publ. on Feb. 27, 2008.

32 Patent CN 100367953 C, IPC: A61K 31/352; A61K 9/10; A61K 9/127; A61K 9/14; A61P 29/00; A61P 35/00; A61P 37/08; A61P 39/06, A61P 7/06, publ. on Feb. 13, 2008.

33 Patent CN 102058536 A, IPC: A61K 31/352; A61K 47/48; A61K 9/127; A61P 11/00, publ. on May 18, 2011.

34 Patent CN 101904821 A, IPC: A61K 31/352; A61K 9/16; A61K 9/19; A61K 9/20; A61K 9/48; A61P 29/00; A61P 3/06; A61P 35/00; A61P 37/08, A61P 39/06, A61P 7/02; A61P 9/10; publ. on Dec. 8, 2010.

35 Patent of Ukraine UA 76393, IPC: A61K 9/127; 31/353; A61K 47/44; A61P 31/06; A61P 31/00; A61P 35/00, опу опубл. π. Jul. 17, 2013.

36 Patent of Ukraine UA 111762. IPC: A61K 9/127; 31/353; A61K 47/44; A61P 39/06; A61P 9/10; A61P 27/02. A method for producing a pharmacologically active liposomal agent comprising quercetin/Hryhorieva G. S., Krasnopolskyi Yu. M., Konakhovych N. F., Pasechnykova N. V., publ. on Jun. 10, 2016, Bul. No. 11.

37 Compendium 2019. Drugs. Lipoflavon®. Instruction. UA/3581/01/01. https://compendium.com.ua.

38 Quercetinum, PVP Sociedade Anonima, BR.

39 Quercetinum, Alfa Aesar GmbH & CoKG, DE.

40 Phosphatidylcholine, Lecithin-standard UA/13014/01/01.

41 Phosphatidylcholine, Lipoid E PS S, DE.

42 The State Pharmacopoeia of Ukraine, —2001— Kharkiv—531 p., page 756.

43 Zinc chloride: Sigma-Aldrich. CAS Number 7646-85-7. Sources No. 38-41 and No. 43 are only references to substances that may have been used in the Application, indicating examples of typical manufacturers.

44 European Convention for the Protection of Vertebrate Animals used for Experimental and Other Scientific Purposes as of Mar. 18, 1986: Verkhovna Rada of Ukraine, official web portal: International documents (Council of Europe).

45 Stefanov O. V. Preclinical studies of medicinal products (guidelines). Edited by O. V. Stefanov-K.: Avicenna, 2001. —528 p. The reference refers to the preclinical study of non-steroidal anti-inflammatory drugs described in this book, starting on page 292 and continuing on pages 293, 188-300. 292 and then on pages 293, 298-300.

46 Zhang Y., Wen Z., Guan L., Jiang P., Gu T., Zhao J., Lv X., Wen T. Extracellular histones play an inflammatory role in acid aspiration-induced acute respiratory distress syndrome. Anesthesiology. 2015 January; 122(1): 127-139.

47 Pomytkin I. A., Karkischenko V. N., Fokin Yu. V., Nesterov M. S., Petrova N. V. A fatal model of acute lung injury and acute respiratory distress syndrome. Biomedicina. 2020; 16(4). —p. 24-33.

The invention claimed is:

1. A pharmacologically active liposomal composition for treating an acute respiratory distress syndrome, the composition comprising phosphatidyl choline, quercetin, lactose, and zinc chloride at a ratio of content of phosphatidyl choline:quercetin:zinc ion in liposomes being from 1:0.027:0.002 to 1:0.027:0.023 wherein the composition is a lyophilized powder having a ratio of components (wt. %) as follows:

quercetin—1,
phosphatidyl choline—36.7,
zinc ion—0.11-0.43,
lactose—54.51,
remainder—water, chloride ion.

2. The composition according to claim 1, wherein it is suitable for preparation of an emulsion for inhalation and/or injection use.

3. A method for treating an acute respiratory distress syndrome, the method comprising administering to a subject an effective amount of the composition of claim 1 and a pharmaceutically acceptable excipient and/or carrier.

4. The method of claim 3, wherein the subject has an acute respiratory distress syndrome.

* * * * *